(12) United States Patent
Mohapatra et al.

(10) Patent No.: US 10,576,100 B2
(45) Date of Patent: Mar. 3, 2020

(54) CHITOSAN ZINC OXIDE NANOPARTICLE FORMULATION FOR TREATING DRUG RESISTANT BACTERIA

(71) Applicants: Shyam S. Mohapatra, Lutz, FL (US); Alya Limayem, Tampa, FL (US)

(72) Inventors: Shyam S. Mohapatra, Lutz, FL (US); Alya Limayem, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 16/159,838

(22) Filed: Oct. 15, 2018

(65) Prior Publication Data

US 2019/0030065 A1    Jan. 31, 2019

Related U.S. Application Data

(60) Division of application No. 15/800,841, filed on Nov. 1, 2017, now Pat. No. 10,179,146, which is a continuation-in-part of application No. 15/298,832, filed on Oct. 20, 2016, now abandoned.

(60) Provisional application No. 62/243,877, filed on Oct. 20, 2015.

(51) Int. Cl.
| | | |
|---|---|---|
| A61K 31/722 | (2006.01) | |
| A61K 9/107 | (2006.01) | |
| A61K 33/30 | (2006.01) | |
| C02F 1/50 | (2006.01) | |
| A61K 47/24 | (2006.01) | |

(52) U.S. Cl.
CPC .......... *A61K 31/722* (2013.01); *A61K 9/1075* (2013.01); *A61K 33/30* (2013.01); *A61K 47/24* (2013.01); *C02F 1/50* (2013.01); *C02F 2303/04* (2013.01); *C02F 2305/08* (2013.01)

(58) Field of Classification Search
CPC .... A61K 31/722; A61K 9/1075; A61K 33/30; A61K 47/24; C02F 1/50; C02F 2305/08; C02F 2303/04
See application file for complete search history.

(56) References Cited

PUBLICATIONS

Linayem et al, Nanotherapeutics for the Mutating Multi-drug Resistant Fecal Bacteria, J Nanotec NanoSci, (Year: 2015).*

(Continued)

*Primary Examiner* — Carlos A Azpuru
(74) *Attorney, Agent, or Firm* — Michele L. Lawson; Smith & Hopen, P.A.

(57) ABSTRACT

A broad-based remediation mechanism against MRFs and alternative fecal indicators such as multidrug resistant *Pseudomonas aeruginosa*, including nanotechnology formulations and methodologies that may be used to develop novel treatment strategies against certain drug resistant bacterial strains. The current invention relates to the treatment of drug resistant bacteria from nosocomial infections, for example in hospitals and in food animals. The invention uses hybrid nanomaterials comprising oligo-chitosan and zinc oxide formulated as nanoparticles and micelles. The inventors unexpectedly found unique properties of very small oligomers of chitosan that effectively treat multi-drug resistant bacteria without compromising the balance of the beneficial flora in the physiological and ecological microenvironments in a host. Also, the combination of chitosan with zinc oxide demonstrated synergistic and unexpected effects in remediation of important food-borne bacteria including the resistant types.

13 Claims, 26 Drawing Sheets

Specification includes a Sequence Listing.

(56) References Cited

PUBLICATIONS

Bakhshi S, Padmanjali KS, Arya LS, 2008. Infections in childhood acute lymphoblastic leukemia: an analysis of 222 febrile neutropenic episodes. Pediatr Hematol Oncol 25: 385-392.

Cattaneo C, Quaresmini G, Casari S, Capucci MA, Micheletti M, et al., 2008. Recent changes in bacterial epidemiology and the emergence of fluoroquinolone-resistant *Escherichia coli* among patients with haematological malignancies: results of a prospective study on 823 patients at a single institution. J Antimicrob Chemother 61: 721-728.

Kremery V, Spanik S, Mrazova M, Trupl J, Grausova S, et al., 2002. Bacteremias caused by *Escherichia coli* in cancer patients—analysis of 65 episodes. Int J Infect Dis 6: 69-73.

Limayem A, Donofrio RS, Zhang C, Haller E, Johnson MG, 2015. Studies on the drug resistance profile of Enterococcus faecium distributed from poultry retailers to hospitals, Journal of environmental science and health Part B Pesticides food contaminants and agricultural wastes, 50, 827-832.

Centers for Disease Control and Prevention (CDC), 2013. Antibiotic Resistance Threats in the United States, U.S. Department of Health and Human Services, 1-114.

Lebreton F, van Schaik W, Manson McGuire A, Godfrey P, Griggs A, Mazumdar V, Corander J, Cheng L, Saif S, Young S, Zeng Q, Wortman J, Birren B, Willems RJL, Earl AM, Gilmore MS, 2013. Emergence of Epidemic Multidrug-Resistant Enterococcus faecium from Animal and Commensal Strains. mBio vol. 4 No. 4 e00534-13, 1-10.

Eisenstein BI, Jones GW, 1988. The spectrum of infections and pathogenic mechanisms of *Escherichia coli*. Adv Intern Med 33: 231-252.

Johnson JR, Russo TA, 2002. Extraintestinal pathogenic *Escherichia coli*: "The other bad *E coli*". J Lab Clin Med 139: 155-162.

Orskov I, Orskov F, 1985. *Escherichia coli* in extra-intestinal infections. J Hyg (Lond) 95: 551-575.

Johnson JR, 1991. Virulence factors in *Escherichia coli* urinary tract infection. Clin Microbiol Rev 4: 80-128.

Johnson JR, Kuskowski MA, Gajewski A, Sahm DF, Karlowsky JA, 2004. Virulence characteristics and phylogenetic background of multidrug-resistant and antimicrobial-susceptible clinical isolates of *Escherichia coli* from across the United States, 2000-2001. J Infect Dis 190: 1739-1744.

Johnson JR, Stell AL, 2000. Extended virulence genotypes of Escherichia coil strains from patients with urosepsis in relation to phylogeny and host compromise. J Infect Dis 181: 261-272.

Franz CM, Huch M, Abriouel H, Holzapfel W, Gálvez A, 2011 Enterococci as probiotics and their implications in food safety. Int J Food Microbiol 151: 125-140.

Werner G, Klare I, Heier H, Hinz KH, Bohme G, Wendt M, and Witte W, 2000. Quinupristin/dalfopristin-resistant enterococci of the satA (vatD) and satG (vatE) genotypes from different ecological origins in Germany. Microb Drug Resist 6: 37-47.

Arias CA and Murray BE, 2012. The rise of the Enterococcus: beyond vancomycin resistance. Nat Rev Microbiol 10: 266-278.

Limayem A, 2015. The mutating gastrointestinal flora, multidrug resistant Enterococcus faecium, Agriculture, Food and Analytical Bacteriology, 5: 56-64.

Laukova, A., L. Chrastinova, I. Placha, V. Strompfova, R. Szabóova, K. Cobanova, M. Chrenkova, Z. Formelova, J. Imrichova, J. Ha dryova, L. Ondruska, R. Jurck, R. Ziitnan. 2012. Beneficial effect of bacteriocin-producing strain Enterococcus faecium EF 55 of non rabbit origin in rabbits. In: Hacklander, K. and Thurner, C. Ed. BOKU-Reports on wildlife research and game management. Proc 4th World Lagomorph Conference, Vienna, Austria, Vienna, p. 77.

De Kwaadsteniet, M., S.D. Todorov, H. Knoetze, L.M. Dicks. 2005. Characterization of a 3944 Da bacteriocin, produced by Enterococcus mundtii ST15, with activity against Gram-positive and Gram-negative bacteria. Int. J. Food Microbiol. 105:433-444.

Leroy, F., M.R. Foulquie Moreno, L. De Vuyst. 2003. Enterococcus faecium RZS C5, an interesting bacteriocin producer to be used as a co-culture in food fermentation. Int. J. Food Microbiol. 88:235-240.

Lund, B., C. Edlund. 2001. Probiotic Enterococcus faecium strain is a possible recipient of the vanA gene cluster. Clin. Infect. Dis. 32:1384-1385.

Fisher, K., C. Phillips. 2009. The ecology, epidemiology and virulence of Enterococcus. Microbiol. 155:1749-1757.

Sahoo SK, Parveen S, Panda JJ, 2007. The present and future of nanotechnology in human health care. Nanomedicine 3:20-31.

Arias CA, Murray BE, 2009. Antibiotic-resistant bugs in the 21st century—a clinical super-challenge. N Engl J Med 360:439-443.

Paul S, Seema NP, 2015. In vitro antibacterial potential of chitosan and its derivatives on pathogenic anterobacteriaceae. Natl J Physiol Pharm Pharmacol 5: 119-124.

Reddy KM, Feris K, Bell J, Wingett DG, Hanley C, Punnoose A, 2007. Selective toxicity of zinc oxide nanoparticles to prokaryotic and eukaryotic systems. Appl Phys Lett 90:2139021-2139023.

Jin T, Sun D, Su JY, Zhang H, Sue HJ, 2009. Antimicrobial efficacy of zinc oxide quantum dots against Listeria monocytogenes, *Salmonella enteritidis*, and *Escherichia coli* O157:H7. J Food Sci 74:M46-52.

Dixit S et al., 2013. Phospholipid micelle encapsulated gadolinium oxide nanoparticles for imaging and gene delivery. RSC Adv 3: 2727-2735.

Kumar A, Glaum M, El-Badri N, Mohapatra S, Haller E, Park S, Patrick L, Nattkemper L, Vo D, Cameron DF, 2011. Initial observations of cell-mediated drug delivery to the deep lung. Cell Transplant 20: 609-618.

Premanathan M, Karthikeyan K, Jeyasubramanian K, Manivannan G, 2011. Selective toxicity of ZnO nanoparticles toward Gram-positive bacteria and cancer cells by apoptosis through lipid peroxidation. Nanomedicine. 7:184-92.

Abd Elhady, MM. 2012. Preparation and characterization of chitosan/zinc oxide nanoparticles for imparting antimicrobial and UV protection to cotton fabric. International journal of carbohydrate chemistry, 2012: 6.

Perelshtein I, Ruderman E, Perkas N, Tzanov T, Beddow J, Joyce E, Gedanken, A, 2013. Chitosan and chitosan-ZNO-based complex nanoparticles: formation, characterization, and antibacterial activity. J Mater Chem B 1: 1968-1976.

Limayem, A. et al. Oct. 2015. Nanotherapeutics for mutating multidrug resistant fecal bacteria. J Nanotec Nanosci. vol. 1, Issue 2, KJNN-100106.

Limayem, A. et al. Aug. 2016. Molecular identification and nanoremediation of microbial contaminants in algal systems using untreated wastewater. Journal of Environmental Science and Health, Part B. 51:12, 868-872.

Potara, M. et al. 2011. Synergistic antibacterial activity of chitosan-silver nanocomposites on *Staphylococcus aureus*. Nanotechnology 22:135101 (9pp).

Revathi, T. et al. Mar. 2018. Immobilization of ZnO on Chitosan-Neem seed composite for enhanced thermal and antibacterial activity. Advanced Powder Technology. 29:1445-54.

Al-Dhabaan, F.A. et al. 2017. Chemically-Produced Copper, Zinc Nanoparticles and Chitosan—Bimetallic Nanocomposites and Their Antifungal Activity against Three Phytopathogenic Fungi. International Journal of Agricultural Technology. vol. 13(5):753-69.

Rahman, P.M. et al. Jan. 2017. Flexible chitosan-nano ZnO antimicrobial pouches as a new material for extending the shelf life of raw meat. International journal of biological macromolecules. 97:382-91.

Al-Naamani, L. et al. Oct. 2016. Chitosan-zinc oxide nanocomposite coatings for the prevention of marine biofouling. Chemosphere. 168:408-17.

Chatterjee, P. et al. Feb. 2017. Disinfection of secondary treated sewage using chitosan beads coated with ZnO—Ag nanoparticles to facilitate reuse of treated water. Journal of Chemical Technology & Biotechnology. 92:2334-41.

Al-Naamani, L. et al. Oct. 2016. Chitosan-zinc oxide nanoparticle composite coating for active food packaging applications. Innovative Food Science & Emerging Technologies. 38:231-37.

* cited by examiner

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
agagtttgat cctggctcag                    20

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
ggttaccttg ttacgactt                     19

CHITOSAN ZINC OXIDE NANOPARTICLE FORMULATION FOR TREATING DRUG RESISTANT BACTERIA

CROSS-REFERENCE TO RELATED APPLICATIONS

This nonprovisional application is a divisional of and claims priority to U.S. Non-Provisional patent application Ser. No. 15/800,841, now U.S. Pat. No. 10,179,146, entitled "Compositions and Methods for Mitigating Drug Resistant Bacteria, filed Nov. 1, 2017, which is a continuation in part of and claims priority to U.S. Non-Provisional patent application Ser. No. 15/298,832, entitled "Compositions and Methods for Mitigating Drug Resistant Bacteria", filed Oct. 20, 2016, which is a nonprovisional of and claims priority to U.S. Provisional Patent Application No. 62/243,877, entitled "Compositions and Methods of Mitigating Drug Resistant Bacteria", filed Oct. 20, 2015, both of which are incorporated herein by reference in their entireties.

FEDERALLY SPONSORED RESEARCH OR DEVELOPMENT

This invention was made with Government support under Grant No. CA152005 awarded by National Institutes of Health. The government has certain rights in the invention.

TECHNICAL FIELD

The present application relates, generally, to drug resistant bacteria. More specifically, it relates to nanoparticle formulations that mitigate against multi-drug resistant bacteria from nosocomial infections, for example in hospitals and in food animals.

BACKGROUND

Multidrug resistant gastrointestinal, fecal bacteria (MRF) are proliferating at a considerable rate to reach and impact downstream food chains, as well as hospital settings. MRFs, including gram-negative *Escherichia coli* and gram-positive *Enterococcus faecium* are of prime concern to food safety and public health. While there are several foodborne pathogens originating from animal gut having resistance, MRFs-including Vancomycin Resistant *E. faecium* (VRE)—remain the leading cause of hospital-acquired infections.

Clonal complex resistant strains (CCs) of *Enterococcus faecium*, including mainly the multidrug resistant strain, have emerged as a leading cause of nosocomial pathogens, constituting a serious level of threat that has caused almost 10,000 infections and 650 deaths each year in the U.S. Clonal complex 17 (CC17) is now the primary cause of patient urinary tract and bloodstream infections in hospitals and could further lead to endocarditis and death primarily in immunocompromised populations, along with serious complications primarily in patients with long stay in hospitals.

Conjointly in this pathogenic spread, *Escherichia coli* is implicated in millions of extra-intestinal infections, resulting in more than 100,000 cases of sepsis and 40,000 sepsis-associated deaths. Moreover, the enormous intrinsic capability and phenotypic elasticity of the MRF strains—mainly *E. faecium*—enable them to acquire other genes from the environment, mutate continuously, and transfer genes to other pathogens, including primarily *Salmonella* and *Campylobacter* genera found in food animals. Although some strains of *E. faecium* are used in the food industry and are also known for their probiotic attributes, the tremendous ability of some strains to acquire resistance would be a major bottleneck. It is also quite possible that resistant MRFs from food form a niche in a human's gastrointestinal tract, leading to a reservoir of resistance and consequently jeopardizing the lives of the most immunocompromised populations.

Despite the increasing threat of mutating MRFs, many strains of *E. faecium* are also lactic acid bacteria and are known for their probiotic attributes. They have been extensively added in food for their fermentative ability and health benefits. It has been shown that rabbits in animal husbandries that were given water containing *E. faecium* as a probiotic had higher average weight gains as well as a healthier natural intestinal flora. While *E. faecium* helps prevent antibiotic-associated diarrhea, enhance the immune system, and lower the cholesterol level, other strains are used for their food safety attributes in limiting zoonotic pathogens from food animals through bacteriocin production. Despite their probiotic attributes, the considerable ability of some *E. faecium* strains to mutate in multiple types of environments has made the use of *E. faecium* as a fermentative strain questionable. Furthermore, the continuous use of the traditional antibiotics has led to the induction of "Super Bugs" that are unresponsive to a wide range of antibiotics. Some strains of multidrug resistant fecal bacterial—primarily *Enterococcus*—has exhibited the ability to develop resistance to most, if not all, drugs used against them.

A substantial review on the antibacterial properties of bacteriocins has been implemented by Fisher and Phillips [Fisher, K et al. (2009). The ecology, epidemiology and virulence of *Enterococcus*. Microbiol. 155:1749-1757]. However, the tremendous ability of some strains to acquire virulence genes from other strains and convert into pathogenic strains would hinder the beneficial attributes of *E. faecium*. This is increasingly more problematic due to the considerable ability of *E. faecium* to mutate and acquire virulent genes in multiple types of environment.

In addition to the proliferation of nosocomial and food animal-related MRFs, the presence of multidrug resistant bacteria, including recently recognized alternative fecal indicator *Pseudomonas aeruginosa*[Liang L, et al. (2015). Alternative fecal indicators and their empirical relationships with enteric viruses, *Salmonella enterica*, and *Pseudomonas aeruginosa* in surface waters of a tropical urban catchment. Appl Environ Microbiol 81:850-860.] has been elucidated in municipal wastewaters used for algae cultivation [Limayem A, et al. (2017). Prokaryotic community profiling of local algae wastewaters using advanced 16S rRNA gene sequencing. *Environ Sci Pollut Res*. https://doi.org/10.1007/s11356-017-0078-z; Limayem A, et al. (2016). Molecular identification and nanoremediation of microbial contaminants in algal systems using untreated wastewater. *J. Environ. Sci. Health*., Part B 51(12): 868-872].

Algae biomass-fed wastewater is an emerging cost-effective medium with a multiplicity of uses including but not limited to food in aquaculture, remediation in wastewater treatments, algal lipid production and algal bioenergy manufacture. In regards to bioenergy manufacture specifically, algae biomass-fed wastewaters are increasingly spurring interest among researchers after escalating concerns of climate change due to its ability to act as a $CO_2$ sink, generating a higher yield per acre of biofuel than other natural sources [Von Sivers M., Zacchi G. (1996). Ethanol from lignocellulosics: a review of the economy. Bioresour Technol. 56:131-140.; Goldemberg J. (2007). Ethanol for a sustainable energy future. 315: 808e10.].

Wastewaters provide delivery of nutrients such as phosphorus and nitrogen but also can host some resistant bacterial strains, which are of prime concern in algae production that is performed under non-aseptic conditions. The algal crop is susceptible to grazing from multidrug resistant *Pseudomonas aeruginosa* and other alternative microorganisms, which would have infectious properties, creating unsafe work conditions. Therefore, a novel natural antibiotic is of dire need for this valuable "green" industry.

Accordingly, what is needed is an effective intervention mechanism/therapy for mitigating or reducing multi-drug resistant bacterial pathogens found in food animals, humans, and the respective environment. As applied to algae biomass-fed wastewaters, what is needed is an integrated system approach to employ molecular and systemic methods to trace multidrug resistant bacterial flora from the source, which requires a complete screening of the predominant prokaryotic groups in algal systems to ensure an efficient nanoremediation. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY

The long-standing but heretofore unfulfilled need for an effective antimicrobial that is natural/non-toxic, durable/sustainable, and cost-effective is now met by a new, useful, and nonobvious invention.

In an embodiment, the claimed subject matter is a nanoparticle formulation for treating multi-drug resistant bacteria (e.g., *Escherichia coli* and/or *Enterococcus faecium*), comprising a combination of a therapeutically effective amount of chitosan oligomers and a therapeutically effective amount of zinc oxide nanoparticles (e.g., ~80.34% zinc and ~19.6% oxygen, surface area of 54 $m^2/g$), wherein the combination is disposed in a pharmaceutically acceptable carrier and is selectively toxic against the multi-drug resistant bacteria. The pharmaceutically acceptable carrier may be a nanomicelle composition, including the zinc oxide nanoparticles outlined by a hydrophobic shell formed of anionic lipid micelles with a chitosan coating. The anionic lipid micelles may further include 1,2-dioleoyl-sn-glycero-3-phosphate. In certain embodiments, the chitosan can have a molecular weight of about 3 kDa to about 50 kDa, with particular effectiveness observed at approximately 3 kDa. In other embodiments, the molecular weight can be about 10 kDa with a surface area of about 4.56-0.74 $m^2/gL$. The combination of the zinc oxide and chitosan may have an average minimum inhibitor concentration of about 0.781 mg/mL to about 1.302 mg/mL.

In a separate embodiment, the current invention is a method of treating wastewater for algae biomass cultivation, comprising contacting with the wastewater a combination of an effective amount of chitosan oligomers and an effective amount of zinc oxide nanoparticles, wherein the combination inhibits lytic bacteria (e.g., *Pseudomonas aeruginosa, Bacillus pumilus, Bacillus safensis, Cellulosimicrobium cellulans, Micrococcus luteus,* and *Staphylococcus epidermidis*) without affecting algal viability in the wastewater. Particular effectiveness of the combination of the zinc oxide and chitosan was observed when chitosan had a molecular weight of about 10 kDa.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 6A depicts *E. coli* BAA-2471 exposed to zinc oxide nanoparticles and chitosan for 16 hours. The bacterium on the left shows chitosan adsorbed to the cell membrane and zinc oxide nanoparticles attached to the membrane. Low electron density indicates that the bacterium is lysing. An intact *E. coli* BAA-2471 is on the right.

FIG. 6B depicts *E. coli* BAA-2471 exposed to chitosan and zinc oxide nanoparticles, showing adsorption of chitosan to cell membrane of bacteria and adherence of zinc oxide to bacteria. ZnO is causing pitting of the bacterial membrane.

FIG. 6C depicts *E. faecium* 1449 exposed to chitosan and zinc oxide. An intact *E. faecium* 1449 is in the lower left. Small high-density regions inside the cell are indicative of the nanoparticles. Presence of asterisk-like fragments detail lyses and disintegration of the cell wall.

FIG. 6D is a higher magnification photograph of the disintegration of the cell wall of *E. faecium*.

FIG. 6E depicts a resistant co-culture, MRF of *E. faecium* 1449 and *E. coli* BAA-2471 subjected to the combinatory nanoparticles. Nanoparticles surrounding the outside of the cells demonstrate clearly the formation of a synergistically formed meshing. Lower electron density indicates lyses of the bacteria, which is noticeable in both bacterial strains though notably more soon *E. coli* BAA-2471 in this panel.

FIG. 6F is a higher magnification photo of the co-cultured MRFs detailing the presence of nanoparticles surrounding and inside both bacterial species.

FIG. 8A depicts *Bacillus* species exposed to zinc oxide nanoparticles and chitosan for 24 h. Low electron density indicate that a bacterium is lysing. High electron density within the lysing cells as indicated by the red arrow is representative of the nanoparticles inside the cell.

FIG. 8B depicts *Bacillus* culture exposed to chitosan and zinc oxide nanoparticles, showing adsorption of chitosan within the dying cell and adherence of the nanoparticle "meshing" to bacteria. A living cell of high electron density is visible to the right.

FIG. 8C depicts *M. luteus* subjected to the combinatory nanoparticles. The cell noted by the red arrow in the bottom of the cluster appears shriveled and its cell wall is forming protrusions. The nanoparticle meshing is visible at the top middle of the image.

FIG. 8D is a broader magnification photo of *M. luteus* detailing lysis of multiple cells. The low electron density of the cells indicates the cells are dying. Small high-density particles are distinctive of the nanoparticles inside the lysed cell. High level of cellular protrusions indicates extensive damage to the Gram-positive cell wall.

FIG. 8E depicts a dying *Pseudomonas* cell. To the left, living *M. luteus* cells are present for reference. The red arrow points to a high electron density structure representing the nanoparticles within the bacterial cell. The low electron density of the cell indicates that the nanoparticles are degrading and damaging the cell membrane of the Gram-negative bacteria.

FIG. 8F depicts a single *Pseudomonas* cell above a series of dying, bottom left, and intact *M luteus* cocci. The high electron density cocci species near the *Pseudomonas* cell are used as a reference. The cell indicated by the red arrow demonstrates the process of lysis when compared to the surrounding cells despite moderate electron density.

DETAILED DESCRIPTION

Figure 1:
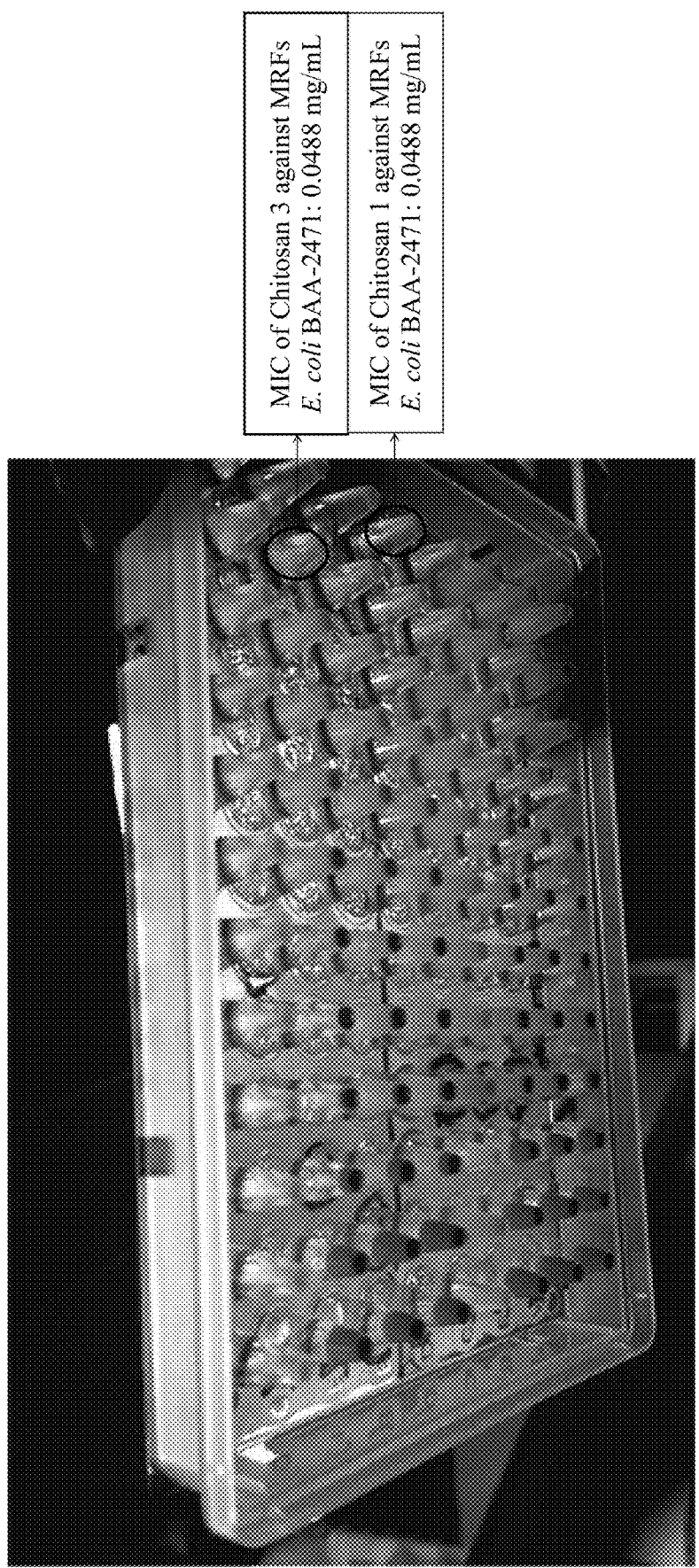
FIG. 1 depicts a Minimum Inhibitory Concentration (MIC) test of chitosan alone against multidrug resistant fecal bacteria (MRF) strains of Gram-negative *Escherichia coli* BAA-2471 and Gram-positive *Enterococcus faecium* 1449.

In the following detailed description, reference is made to the accompanying drawings, which form a part thereof, and within which are shown by way of illustration specific embodiments by which the claimed subject matter may be practiced. It is to be understood that other embodiments may be used and structural changes may be made without departing from the scope of the claimed subject matter.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

In certain embodiments, the present application describes a broad-based remediation mechanism against MRFs and includes nanotechnology formulations and methodologies that may be used to develop novel mitigation strategies against these drug resistant strains. In an embodiment, the claimed subject matter relates to mitigation of drug resistant bacteria from nosocomial infections, for example in hospitals and in food animals. The claimed subject matter uses hybrid nanomaterials comprising oligo-chitosan and zinc oxide formulated as nanoparticles and micelles.

The present application describes the development of a targeted-nanoremediation against MRFs, which until this point has remained a dire unmet need. The combination of chitosan oligomers and ZnO nanoparticles (CZNPs) have an extraordinary antimicrobial potential compared to either agent alone and can be useful against a myriad of MRF strains from agricultural systems encompassing wastewaters and food animals to medical devices (i.e., indwelling catheter) beyond hospital patients and settings. Additionally, as we demonstrated in Limayem et al. 2016 and Limayem et al. 2017[Limayem A, et al. (2017). Prokaryotic community profiling of local algae wastewaters using advanced 16S rRNA gene sequencing. *Environ Sci Pollut Res*. https://doi.org/10.1007/s11356-017-0078-z; Limayem A, et al. (2016). Molecular identification and nanoremediation of microbial contaminants in algal systems using untreated wastewater. *J. Environ. Sci. Health*., Part B 51(12): 868-872], CZNPs has shown effectiveness against a broad spectrum of harmful multi-drug resistant (MDR) bacteria and their biofilms which are not MRF-inclusive, including some emerging strains of MDR *Pseudomonas aeruginosa* and *Micrococcus* genera found abundantly in municipal wastewaters [Limayem A, et al. (2017). Prokaryotic community profiling of local algae wastewaters using advanced 16S rRNA gene sequencing. *Environ Sci Pollut Res*. https://doi.org/10.1007/s11356-017-0078-z]. Ultimately, CZNPs agent shows advantageous effects not only on MRFs but also against other multi-drug resistant biofilms and has great potential to be used both in vitro and in vivo.

As will be shown herein, the inventors unexpectedly found unique properties of very small oligomers of chitosan that effectively mitigate MRFs- and Vancomycin-resistant *Enterococci* (VRE)-induced illnesses without compromising the balance of the beneficial flora in the abdomen. Also, the combination of chitosan with ZnO demonstrated synergistic and unexpected effects in remediation of important food-borne bacteria including the resistant types. The studies, discussed further as this specification continues, investigates the means of remediation of multi-drug resistant bacteria. In the studies, the antibacterial properties of polymeric chitosan-based nanoparticles and/or ZnO was investigated. The results show that very small oligomers of chitosan effectively mitigate MRFs and VRE. The results demonstrate that chitosan oligomeric nanoparticles by themselves or in combination with ZnO provide for the effective remediation of MRFs and VRE.

Selection of Chitosan and Zinc Oxide

A natural antimicrobial that is non-toxic and sustainable was deemed of prime interest. Chitosan, arguably the most important derivative of chitin, is emerging as a strong, natural antimicrobial that is considered safe for human health. Additionally, chitosan with its exposed amino groups (~NH2 groups) is involved in specific interactions with metals, which allows chitosan to behave differently from other polysaccharides due to the positive charge on its surface. In a solid state, chitosan is a semicrystalline polymer that is soluble in acidic solutions. However, its solubility depends on the distribution of acetyl groups along its polysaccharide chain and the molecular weight. Chitosans have proven to be effective as an antibacterial against a variety of pathogens namely gram-negative strains and biofilms [Arias C A, Murray B E (2009) Antibiotic-resistant bugs in the 21st century—a clinical super-challenge. N Engl J Med 360:439-443]. The effectiveness of such antibacterial activity was found to be correlated with chitosan's molecular weight, thus allowing the chitosan biopolymers to be highly effective when compared to chitosan oligomers, which were significantly smaller.

In addition, ZnO is emerging as an effective nanocomponent for its effectiveness against some cancer cells, in addition to its potential for mitigating some gram-positive strains with regard to its selective toxicity [Limayem, A. et al. Nanotherapeutics for mutating multi-drug resistant fecal bacteria. J. Nanotec Nanosci. 2015, 1, 100-106]. On the other hand, ZnO nanoparticles seem to inhibit or cause bacterial death more efficiently when they are smaller in size but higher in concentration. A smaller size at higher concentrations provides higher specific surface areas and facilitates the penetration of the antimicrobial agent into the bacterial membrane.

Toxicity of Zinc Oxide and Chitosan

ZnO nanoparticles and chitosan nanoparticles have been tested in several studies for cytotoxic properties to determine the lowest margin of safety to human and animal cells. ZnO nanoparticles have cytotoxic properties, which improve with a decrease in nanoparticle size. Additionally, the cytotoxic effects of nanoparticles are generally accentuated through oxidative stress. The no-observed-adverse-effect level (NO-AEL), reference dose (RfD), maximum systemic exposure dose (SED) and lowest margin of safety of ZnO nanoparticles was estimated to be 268.4, 2.68, 0.5988, and 448.2 mg/kg/day, respectively [Kim, K., et al. (2017). Risk assessment of zinc oxide, a cosmetic ingredient used as a UV filter of sunscreens. *Journal Of Toxicology & Environmental Health: Part B*, 20(3), 155; Seok, S. H., et al. 2013. Rat pancreatitis produced by 13-week administration of zinc oxide nanoparticles: Biopersistence of nanoparticles and possible solutions. *Journal of Applied Toxicology* 33:1089-96]. Overall, as indicated by recent acute, subacute and chronic studies, the ZnO compound is virtually non-toxic in animal models.

Toxicity levels of chitosan are mainly determined by the degree of acetylation (DD) and the molecular weight; a higher DD value can suggest that the toxicity level is related to both the concentration and molecular weight whereas a low DD value diminishes the relationship. Chitosan uptake is determined by the interaction of its positive charge with the cells in the environment. Particle size is a greater contributor to chitosan's toxicity than concentration. Overall, chitosan was determined to be a relatively non-toxic molecule, with its toxicity depending largely on its purity as certain contaminants can result in harmful effects.

Selective Toxicity of Chitosan-Zinc Oxide Nanoparticles (CZNPs)

Recent studies revealed that chitosan serves as an effective drug-delivery system due to its poly-cationic nature and ability to bind easily to metal oxides [Chopra H and Ruhi G, (2016). Eco friendly chitosan: An efficient material for water purification. The *Pharma Innovation Journal* 5(1): 92-95], such as ZnO. Although particle size is a major factor for determining the toxicity of chitosan, regardless of particle size, chitosan nanoparticles were found to be non-toxic at low concentrations between 10-100 μg/mL, and non-toxic against eukaryotic cells at higher concentrations while simultaneously showing successful antimicrobial properties against Gram-negative bacteria at concentrations of 1.875 mg/ml. ZnO nanoparticles also proved to be selective in prokaryotic and eukaryotic systems; 13 nm ZnO nanoparticles eliminated Gram-negative *E. coli* at concentrations less than 3.4 mM and prevented growth of *S. aureus* at concentrations less than 1 mM, while showing no effect of human T cells [Reddy K M, et al. 2007. Selective toxicity of zinc oxide nanoparticles to prokaryotic and eukaryotic systems. Appl Phys Lett 90:2139021-2139023].

Hence, both chitosan and ZnO are efficient antimicrobial agents for their expression of selective toxicity that is attributed to their molecular charges and structure. The development of a nanomicelle that combines these two antimicrobial agents provides a synergistic effect that increases antimicrobial activity at a lower dosage of both particles. Recent studies have utilized CZNPs as a coating on polyethylene films in food packaging, preventing 99.9% of viable pathogenic bacteria including strains of *E. coli, S. enterica* and *S. aureus* from contaminating food [Al-Naamani, L. et al., (2016). Chitosan-zinc oxide nanoparticle composite coating for active food packaging applications. *Innovative Food Science And Emerging Technologies*, 38(Part A), 231-237]. Additionally, CZNPs were seen to have little to no cytotoxicity, resulting in mild inflammatory responses in mice, and were proven less toxic than ZnO alone with reference to zebrafish embryo survival [Zhang, S. et al., (2016). Biocompatible nanocarriers that respond to oxidative environments via interactions between chitosan and multiple metal ions. *International journal of nanomedicine*, 11, 2769; Girigoswami, K. et al., (2015). Studies on polymer-coated zinc oxide nanoparticles: UV-blocking efficacy and in vivo toxicity. *Materials Science and Engineering: C*, 56, 501-510]. Thus, CZNPs are a justified antimicrobial agent to potentially combat multi-drug resistant bacteria, as will be discussed and evidenced herein through the following studies.

Experiment/Study 1 (Mitigation of Drug Resistant Bacteria)

The nosocomial MRF, Gram-negative-*Escherichia coli*, and Gram-positive-*Enterococcus faecium* are of prime concern to public health safety. This study was performed to examine effectiveness of a natural nanomicelle-based chitosan having different molecular weight and non-toxic ZnO combination to treat these MRF strains in vitro and in vivo. Herein, the antimicrobial effects of nanoparticles (NPs) of chitosan alone, ZnO alone, and chitosan and ZnO (CZNPs) in combination at 1:1 were examined on co-cultured MRFs through the MIC test according to National Committee for Clinical Laboratory Standards (NCCLS). To improve the stability and activity of CZNPs, a carrier system was initially developed comprising PEG-functionalized phospholipid micelles, using either gadolnium oxide in core and MnO with Dox in the core along with the DNA and chitosan on shell.

Results indicated that chitosan (C1 and C2) alone was ineffective at a concentration less than 5 mg/ml against either strains of bacteria as well as against the co-culture. However, C1 and C3 displayed a significant effect on the resistant E. coli BAA-2471 with an MIC of 0.0488 for C1 and beyond 0.0488 for C3. Results further indicated that zinc oxide alone only showed effectiveness against E. faecium at a concentration of 3.125 mg/mL (minimal average MIC of 0.391 mg/mL).

However, surprisingly, the MRF co-culture, E. coli BAA-2471 and E. faecium 1449 was completely inhibited by the CZNPs with an average minimal MIC of 0.781 mg/mL (low MW chitosan 1 of 3 KDa), and an average maximal MIC of 1.302 mg/mL (high MW chitosan 3 of 50 KDa). Synergism of CZNPs proved to be effective against MRF co-culture. This synergistic effect of chitosan and ZnO has proven to be far greater than what would be expected by a combination of the two.

A. Materials and Methods i. Sample Collection and Culture Conditions

The MRF, Gram-negative, E. coli ATCC; BAA-2471 purchased from ATCC and Gram-positive E. faecium 1449 provided by Moffitt Cancer Center were used as target bacteria for this study. These MRF strains were selected for their broad-spectrum resistance and virulence. Only tigecycline was effective against these strains. The above isolates were cultured on Tryptic Soy Agar (TSA) and Tryptic Soy Broth (TSB) (Sigma, St. Louis, Mo.) and incubated at 37° C. for 24 hours and maintained at 37° C. for 24 hours. Bacterial growth was prepared by adding 100 µL fresh culture having $9.5 \times 10^8$ Colony Forming Units (CFU) on Tryptic Soy Agar (TSA) plates.

The chitosan nanoparticles with three different MWs were provided by Dr. Mohapatra's Lab, College of Pharmacy at the University of South Florida (gift of TRANSGENEX NANOBIOTECH Inc., Tampa). The ZnO was purchased from Sigma (SIGMA, St. Louis, Mo.).

ii. Serial Dilution and Plate Counts

Single colonies of E. coli BAA-2471 and E. faecium 1449 were inoculated from TSA plate to 15 mL TSB broth (Sigma, St. Louis, Mo.), respectively. Each broth culture was incubated at 37° C. for 24 hours. A seven times tenfold series dilution was performed by serially diluting 100 µL bacteria broth culture into 900 µL TSB. The 100 µL of each dilution was plated on TSA and incubated at 37° C. for 24 hours.

iii. Synthesis of CZNPs

The synthesis of CZNPs was performed using zinc oxide (ZnO) outlined by hydrophobic shell made up of anionic lipid micellar (DOPA (1,2-dioleoyl-sn-glycero-3-phosphate); Avanti Polar lipid, Inc.) along with chitosan coating. The hydrophobic ZnO was made up of 80.34% zinc and 19.6% oxygen and the surface area was 54 m²/g (MW: 20 nm). The other physical properties of ZnO core shell included acidity/basicity: 6.5-7.0; zeta potential: 9.5 mV-10 mV, crystallinity: Zincite, hexagonal wurtzite. On the other hand, chitosan coat shell contains a 10 kDa molecular weight with 4.56-0.74 m²/gL surface area. The other physical properties of the chitosan coat shell include, zeta potential: 36 mV-40 mV, acidity/basicity: 6.2-7.0, surface porosity: 89.3% and viscosity: 90%. Both particles were mixed in dissolving in 1% (v/v) acetic acid. The nanoparticles were kept in temperature below 25° C.

iv. MIC Assays

These overnight bacteria cultures were diluted 1 in 1,000 in fresh TSB or LB. Sterile 96-well plates were loaded with a co-cultured E. coli BAA-2471 and E. faecium 1449 ($5 \times 10^5$ cfu/mL) and screened against chitosan, ZnO alone and CZNPs at decreasing concentrations by 1:2 dilution to equal a total volume of 100 µL in each of the wells. All assays were performed in triplicate with identical results. Care was taken to not add more than 1.0% CZNPs to any well. The plates were then incubated at 37° C. overnight. The MICs were determined after 24 hours by visual determination of the minimum concentration of compound to inhibit growth. Inhibition of growth was determined by lack of turbidity in the wells.

B. Chitosan Alone (FIG. 1)

50 uL TSB were loaded in 96-well microplates. 50 uL of 20% chitosan solution were added in the first well. The antimicrobial concentrations were decreased by 1:2 dilution with transferring 50 uL to the next well (up to 12 wells). The 50 uL of 6 different bacteria cultures (MRFs, WT and co-cultures) were added in each well. Finally, the concentration of chitosan in the first well was 5%. The plates were then incubated at 37° C. for 24 hours. The MICs were determined by visual determination of the minimum concentration of compound to inhibit growth. Inhibition of growth was determined by lack of turbidity in the wells.

The antimicrobial efficacies of chitosan tested after 24 hours incubation at 37° C. are shown in Table 1. Chitosan 1 and 3 was not effective against both E. faecium culture and the co-culture as well as their WT cultures. However, chitosan 1 and 3 showed a significantly inhibitory antimicrobial ability (0.0488 mg/mL) against multidrug resistant E. coli BAA-2471 culture but was not effective against WT E. coli MCC 13 culture.

TABLE 1

MIC of chitosan sizes 1 (3 kDa) and 3 (50 kDa) against multidrug resistant fecal flora and their wild type (WT) counterparts. Both chitosans were only effective against MRF E. coli strain.

| | Antimicrobial NPs | Chitosan 1 (3 KDa) | Chitosan 3 (5 KDa) |
|---|---|---|---|
| | MIC presented in mg/mL | | |
| MRFs | Escherichia coli BAA-2471 | <0.0488 | 0.0488 |
| | Enterococcus faecium 1449 | ND (>50) | ND (>50) |
| | Co-culture of BAA-2471 and 1449 | ND (>50) | ND (>50) |
| WT | Escherichia coli MCC 13 (WT) | ND (>50) | ND (>50) |
| | Enterococcus faecium ATCC 35667 (WT) | ND (>50) | ND (>50) |

TABLE 1-continued

MIC of chitosan sizes 1 (3 kDa) and 3 (50 kDa) against multidrug
resistant fecal flora and their wild type (WT) counterparts.
Both chitosans were only effective against MRF *E. coli* strain.

| Antimicrobial NPs | Chitosan 1 (3 KDa) | Chitosan 3 (5 KDa) |
|---|---|---|
| Co-culture of MCC 13 and ATCC 35667 (WT) | ND (>50) | ND (>50) |

*ND = Not Detected
MRFs = Multidrug Resistant Fecal Bacteria (*Escherichia coli* BAA-2471 and *Enterococcus faecium* 1449)
WT = Wild Type (*Escherichia coli* MCC 13 and *Enterococcus faecium* ATCC 35667)

Figure 2:
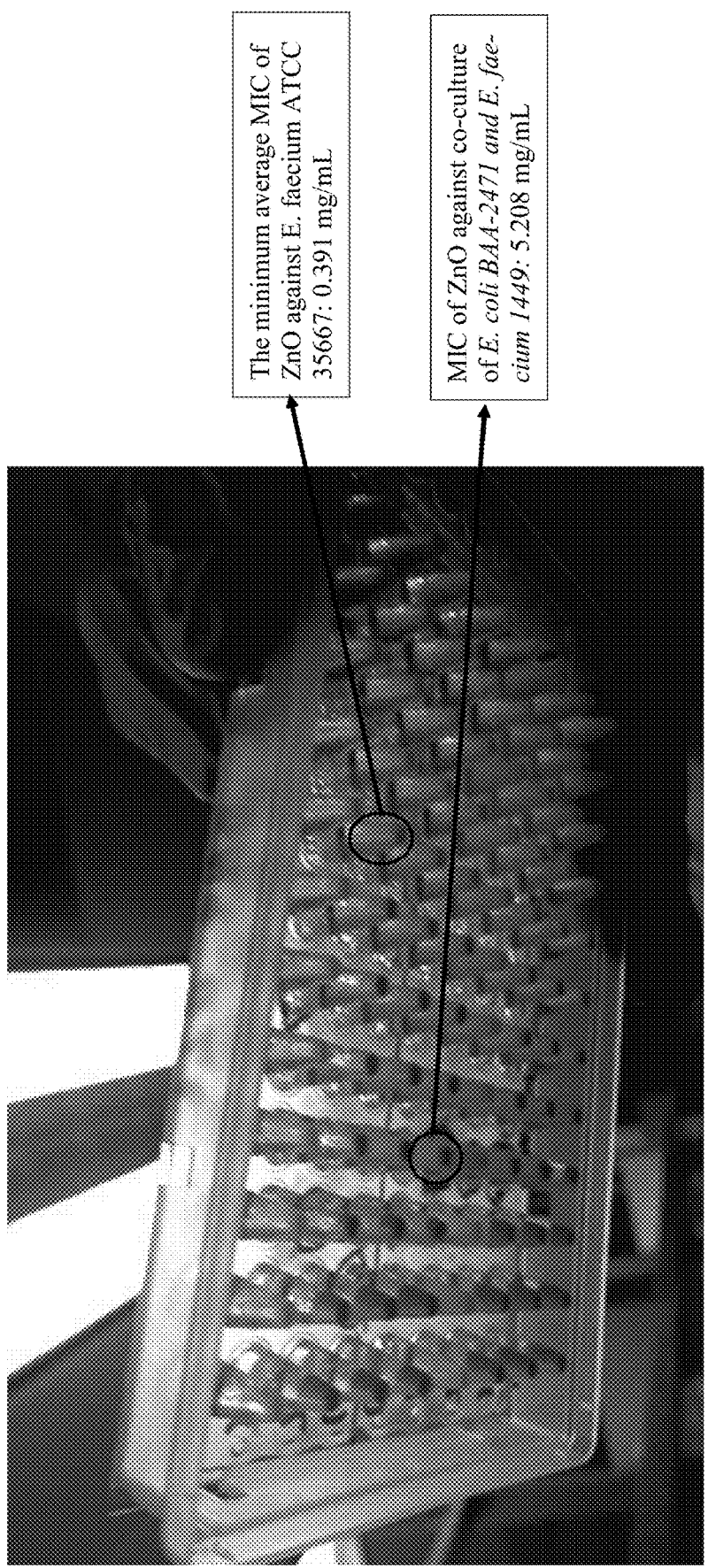
FIG. 2 depicts a MIC test of ZnO alone against MRF strains of Gram-negative *E. coli* BAA-2471 and Gram-positive *E. faecium* 1449.
Figure 3:
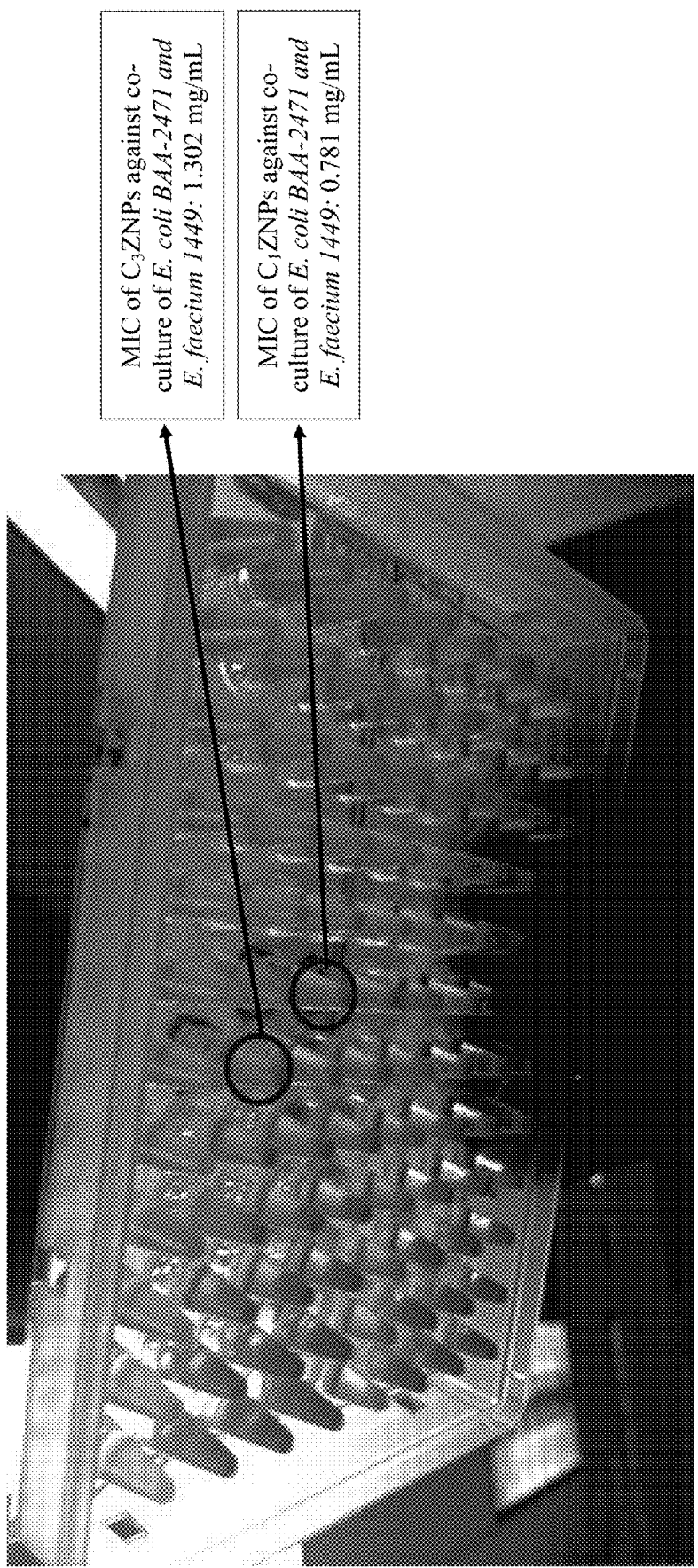
FIG. 3 depicts a MIC test of synergism of chitosan and ZnO (CZNPs) against co-culture of MRF strains of Gram-negative *E. coli* BAA-2471 and Gram-positive *E. faecium* 1449.

C. ZnO Alone (FIG. 2)

50 uL TSB were loaded in 96-well microplates. 50 uL of 20% ZnO solution were added in the first well. The antimicrobial concentrations were decreased by 1:2 dilution with transferring 50 uL to the next well (up to 12 wells). The 50 uL of 6 different bacteria cultures (MRFs, WT and co-cultures) were added in each well. Finally, the concentration of ZnO in the first well was 5%. The plates were then incubated at 37° C. for 24 hours. The MICs were determined by visual determination of the minimum concentration of compound to inhibit growth. Inhibition of growth was determined by lack of turbidity in the wells.

The MIC values of ZnO tested after 24 hours incubation at 37° C. are shown in Table 2. ZnO exhibited varying MICs against different cultures. According to the results, ZnO was more effective against WT *E. coli* MCC 13 (7.292 mg/mL) and WT *E. faecium* ATCC 35667 (0.391 mg/mL) than resistant *E. coli* BAA-2471 (13.54167 mg/mL) and *E. faecium* 1449 (3.125 mg/mL), respectively. However, ZnO showed a slightly lower MIC of 5.208 mg/mL against resistant co-culture than the WT co-culture with a MIC of 6.25 mg/mL.

TABLE 2

MIC of ZnO against multidrug resistant fecal
flora and their WT counterparts. ZnO was more
effective against both MRF and WT
*E. faecium* strains than it was against *E. coli*.

|  | Antimicrobial NPs | ZnO |
|---|---|---|
|  | MIC presented in mg/mL |  |
| MRFs | *Escherichia coli* BAA-2471 | 13.54167 |
|  | *Enterococcus faecium* 1449 | 3.125 |
|  | Co-culture of BAA-2471 and 1449 | 5.208 |
| WT | *Escherichia coli* MCC 13 (WT) | 7.292 |
|  | *Enterococcus faecium* ATCC 35667 (WT) | 0.391 |
|  | Co-culture of MCC 13 and ATCC 35667 (WT) | 6.25 |

*MRFs = Multidrug Resistant Fecal Bacteria (*Escherichia coli* BAA-2471 and *Enterococcus faecium* 1449)
WT = Wild Type (*Escherichia coli* MCC 13 and *Enterococcus faecium* ATCC 35667)

D. CZNP (FIG. 3)

50 uL TSB were loaded in 96-well microplates. 25 uL of 20% chitosan solution and 25 uL of 20% ZnO solution were added in the first well. The antimicrobial concentrations were decreased by 1:2 dilution with transferring 50 uL to the next well (up to 12 wells). The 50 uL of 6 different bacteria cultures (MRFs, WT and co-cultures) were added in each well. Finally, the concentration of CZNPs in the first well was 5%. The plates were then incubated at 37° C. for 24 hours. The MICs were determined by visual determination of the minimum concentration of compound to inhibit growth. Inhibition of growth was determined by lack of turbidity in the wells.

The synergistic and unexpected antimicrobial efficacies of the combination of chitosan and ZnO tested after 24- and 48-hours incubation at 37° C. are shown in Table 3. Both CiZNPs and C3ZNPs presented markedly higher antimicrobial efficacy against resistant co-cultures than WT co-cultures with a minimal average MIC of 0.781 compared to 2.083 mg/mL, respectively. Furthermore, the effectiveness of the CZNPs complex was closely related to the molecular weight of chitosan. Indeed, the MIC values of CiZNPs against resistant *E. coli* BAA-2471, *E. faecium* 1449 and co-culture were 0.0488, 1.563, and 0.781 mg/mL, respectively. However, the MIC values of C3ZNPs against resistant *E. coli* BAA-2471, *E. faecium* 1449 and co-culture were 0.0488, 1.042, and 1.302 mg/mL, respectively. Interestingly, $C_1ZNPs$ with low MW (3 KDa) were significantly more effective than $C_3ZNPs$ with high MW (50 KDa) against resistant co-culture. The MW was an important factor of NPs to impact the antimicrobial efficacy against bacteria cultures.

TABLE 3

MIC of CZNPs against multidrug resistant fecal flora and
their WT counterparts. The MIC of CZNPs against both
MRF *E. coli* and *E. faecium* is lower than for either chitosan
or zinc oxide alone, demonstrating its synergy and
unexpectedly greater effectiveness.

|  | Antimicrobial NPs | $C_1ZNPs$ | $C_3ZNPs$ |
|---|---|---|---|
|  | MIC presented in mg/mL |  |  |
| MRFs | *Escherichia coli* BAA-2471 | <0.0488 | <0.0488 |
|  | *Enterococcus faecium* 1449 | 1.563 | 1.042 |
|  | Co-culture of BAA-2471 and 1449 | 0.781 | 1.302 |
| WT | *Escherichia coli* MCC 13 (WT) | 2.604 | 2.083 |
|  | *Enterococcus faecium* ATCC 35667 (WT) | 3.125 | 2.604 |
|  | Co-culture of MCC 13 and ATCC 35667 (WT) | 2.083 | 3.125 |

*$C_1ZNPs$ = chitosan 1 + ZnO
$C_3ZNPs$ = chitosan 3 + ZnO
MRFs = Multidrug Resistant Fecal Bacteria (*Escherichia coli* BAA-2471 and *Enterococcus faecium* 1449)
WT = Wild Type (*Escherichia coli* MCC 13 and *Enterococcus faecium* ATCC 35667)

Experiment/Study 2 (Nanotherapeutics for Mutating Multi-Drug Resistant Fecal Bacteria)

The current study was performed to test efficacy of a natural antimicrobial, polymeric chitosan-based nanoparticles combined with ZnO to in situ intervention. Herein, the effects of NPs of chitosan, ZnO alone, and a combination of chitosan and ZnO (CZNPs) at 1:1 were examined on co-cultured nosocomial MRFs and a wild type (WT) through the MIC test conform to National Standards, NCCLS. To elucidate visually the mechanistic effects of NPs alone and CZNPs on MRF and WT strains, Transmission Electronic Microscopy (TEM) was performed. While chitosan 1 ($C_1$) and 2 ($C_2$) alone with a molecular weight of 3 kDa and 50 kDa, respectively inhibited resistant *E. coli* strain (*E. coli* BAA-2471), they were ineffective at a concentration less than 5 mg/mL on either *E. faecium* strains and the co-cultures. ZnO and chitosan alone did not exhibit optimal effects on MRF strains and cultures alone. However, the MRF co-culture, E. coli BAA-2471 and E. faecium 1449 was completely inhibited by the $C_1$ZNPs with an average minimal MIC of 0.781 mg/mL, and a maximal MIC of 1.302 mg/mL. Synergism of $C_1$ZNPs over $C_2$ZNPs proved to be predominantly inhibitive of MRF over WT co-cultures. Further TEM analyses demonstrated attachment and lysis of MRFs at 16 h past treatment. Conclusively, CZNPs inhibit MRF co-cultures and is a promising in vivo intervention agent.

A. Materials and Methods i. Sample Collection and Culture Conditions

The MRF, gram-negative, E. coli BAA-2471 purchased from ATCC and gram-positive E. faecium 1449 provided from Moffitt Cancer Center were used as target bacteria for this study. These MRF strains were selected for their broad-spectrum resistance and virulence. Tigecycline was the only available drug effective against these strains. The above isolates were cultured on Tryptic Soy Agar (TSA) and TSB (Sigma, St. Louis, Mo.) and incubated at 37° C. for 24 hours and maintained at 37° C. for 24 hours. Bacterial growth was prepared by adding 100 uL fresh culture having 9.5×108 Colony Forming Units (CFU) on Tryptic Soy Agar (TSA) plates.

The chitosan nanoparticles with three different MWs were provided by Dr. Mohapatra's lab in College of Pharmacy at USF. The ZnO was purchased from Sigma (Sigma, St. Louis, Mo.).

ii. Serial Dilution and Plate Counts

Single colonies of E. coli BAA-2471 and E. faecium 1449 were inoculated from TSA plate to 15 mL TSB broth (Sigma, St. Louis, Mo.), respectively. Each broth culture was incubated at 37° C. for 24 hours. A seven times tenfold series dilution was performed by serially diluting 100 μL bacteria broth culture into 900 μL TSB. The 100 uL of each dilution was plated on TSA and incubated at 37° C. for 24 hours.

iii. MIC Assays

These overnight bacteria cultures were diluted 1 in 1,000 in fresh TSB or LB. Sterile 96-well plates were loaded with a co-cultured E. coli BAA-2471 and E. faecium 1449 (5×10⁵ cfu/mL) and screened against chitosan, ZnO alone, and CZNPs at decreasing concentrations by 1:2 dilution to equal a total volume of 100 μL in each of the wells. All assays were performed in triplicate with identical results. Care was taken to not add more than 1.0% CZNPs to any well. The plates were incubated at 37° C. overnight. The MICs were determined after 24 hours by visual determination of the minimum concentration of compound to inhibit growth. Inhibition of growth was determined by lack of turbidity in the wells.

iv. TEM Assay

Routine preparation of bacteria by negative staining would require pelleting the bacteria to rinse them to remove growth media protein through rinsing. Exposing unfixed bacteria to high-speed centrifugation could alter damaged surface membrane structure. Aldehydes, typically employed to fix and stabilize bacteria prior to observation in the electron microscope, could not be used to stabilize bacteria, as the aldehydes would crosslink proteins in the growth media to the bacterial surface, obscuring surface damage to the bacterial membranes, if present. A new method of fixing the bacteria in osmium tetroxide prior to pelleting was employed to stabilize the bacterial membranes. Osmium would not crosslink any protein in the culture medium to the bacteria but would preserve the membrane structure of the bacteria throughout the centrifugation process, allowing rinsing to remove the culture media proteins necessary to prepare the bacteria for TEM, and impart electron density similar to that of uranyl acetate or other negative stains used to observe bacteria in the electron microscope.

Aliquots of bacteria in growth media were initially fixed in equal volume of 2% osmium tetroxide in distilled water for 10 minutes at 4° C. Following fixation, the bacteria were rinsed in distilled water and pelleted at 5000 RPM for 10 minutes. This rinse step was repeated three times. A proper dilution of bacteria was obtained to yield approximately 2000-3000 bacteria per drop, and one drop of a sample was applied to a carbon-formvar coated copper grid. The grid was allowed to air dry. This procedure was repeated for each sample. Once dry, the grids were observed and photographed in the electron microscope.

B. Results

Figure 4:
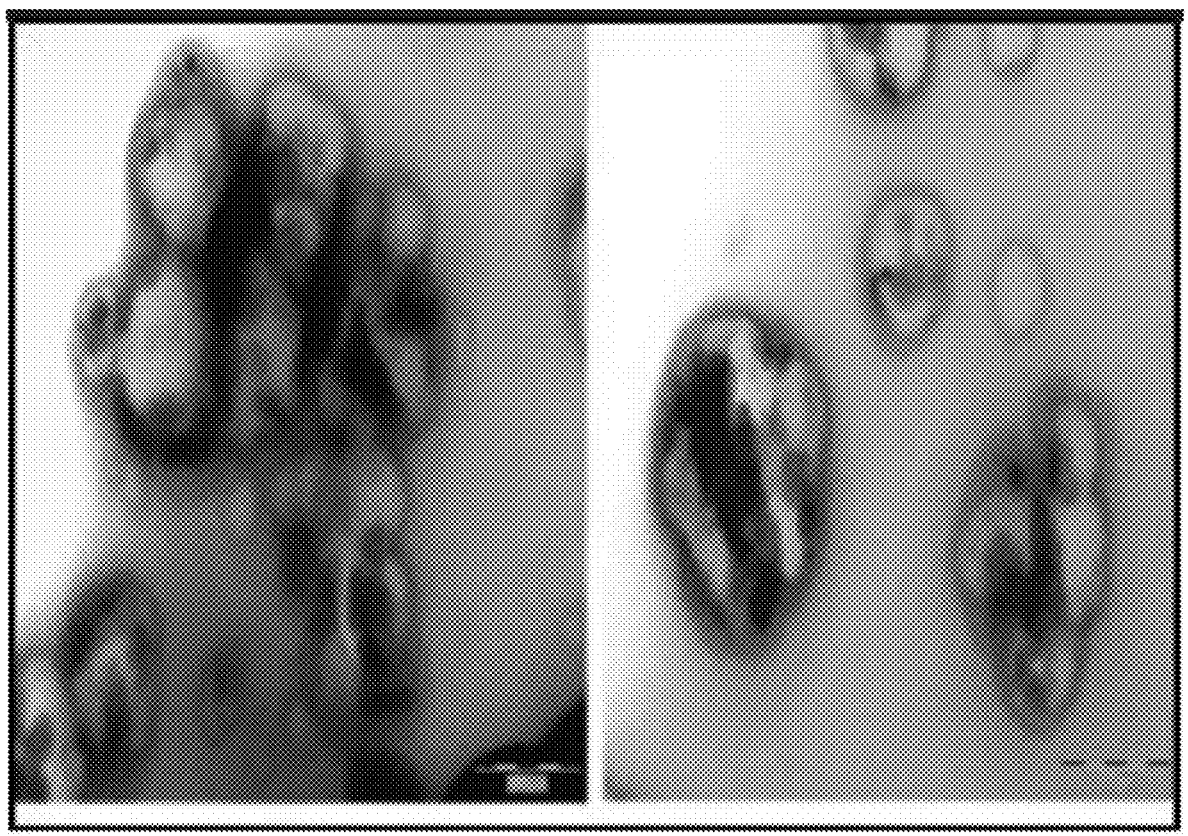
FIG. 4 depicts chitosan particles carrying zinc oxide on the collapsing outer membranes of resistant strains.
Figure 5A:
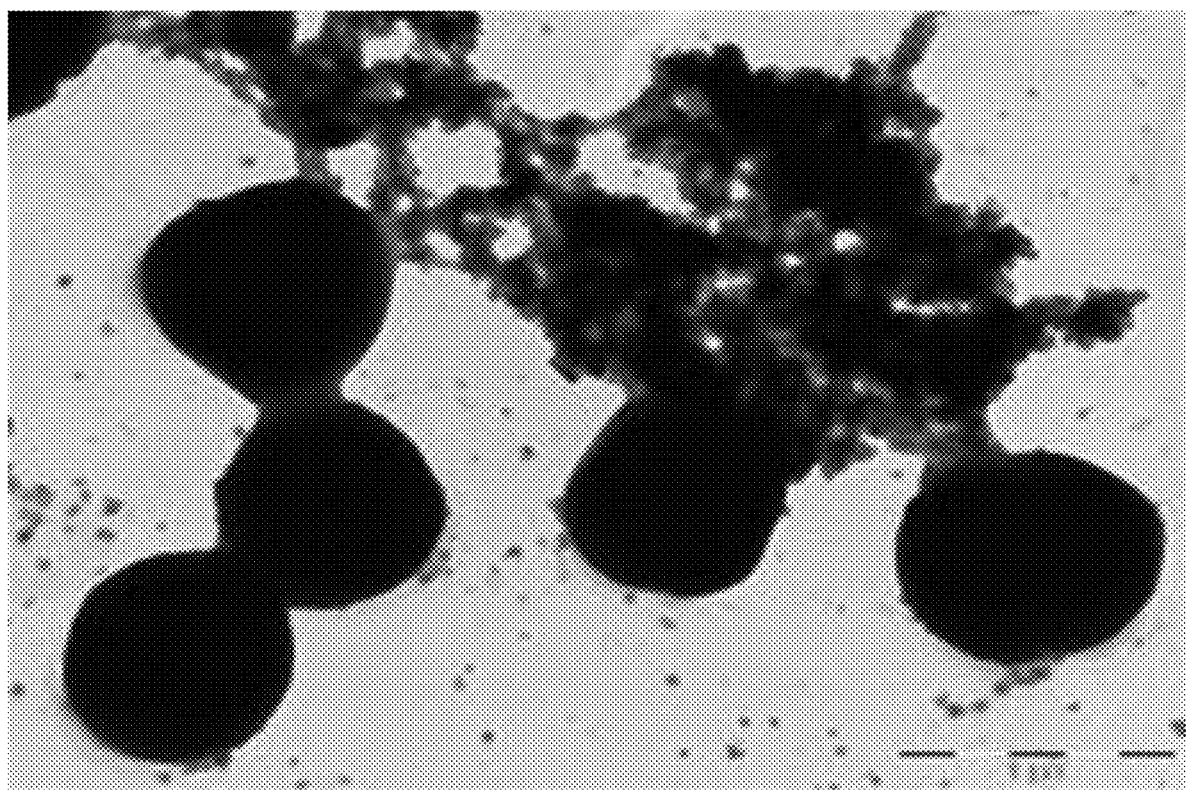
FIG. 5A depicts wild type bacteria in contact with zinc oxide particles, showing no adverse effects from exposure to the zinc oxide at 4 hours.
Figure 5B:
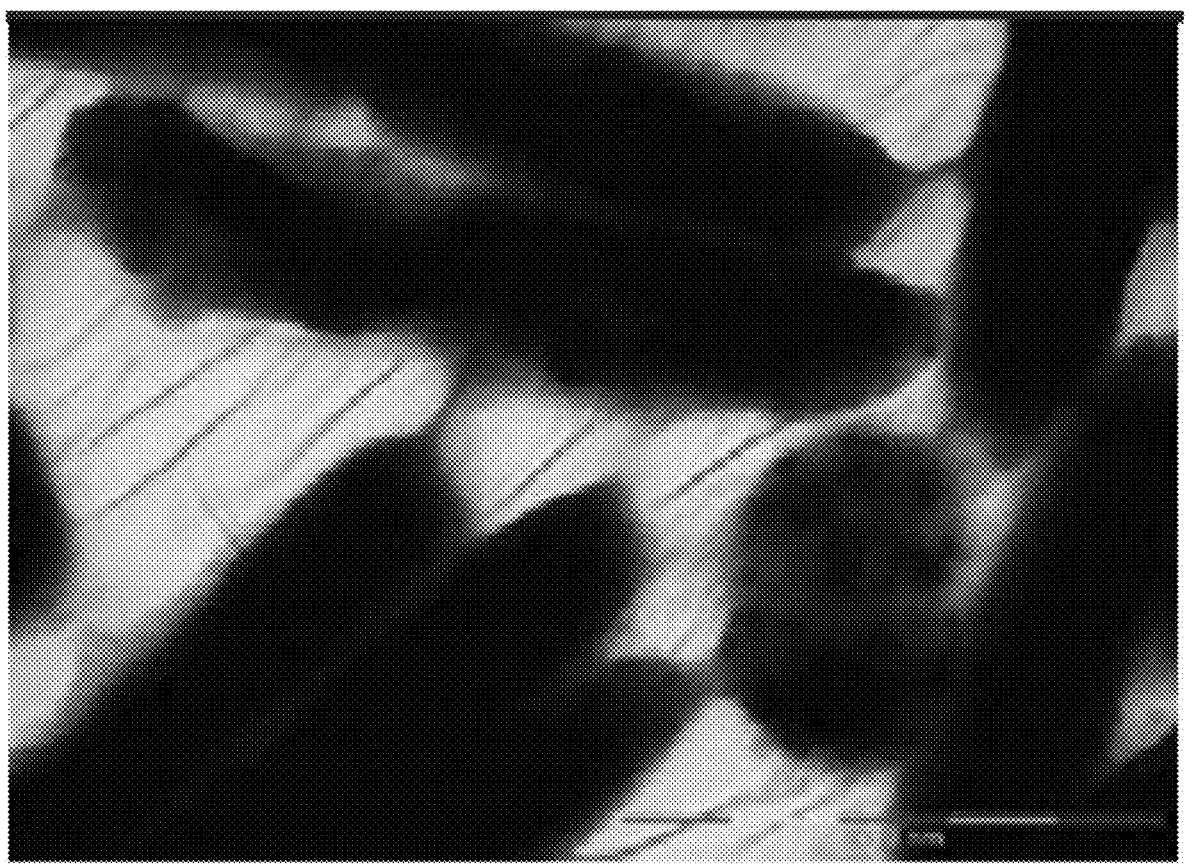
FIG. 5B depicts MRFs including *E. coli* BAA-2471 and *E. faecium* 1449 showing adsorbed chitosan on their cell membranes. The resistant bacteria have begun to lyse and collapse.
Figure 6A:
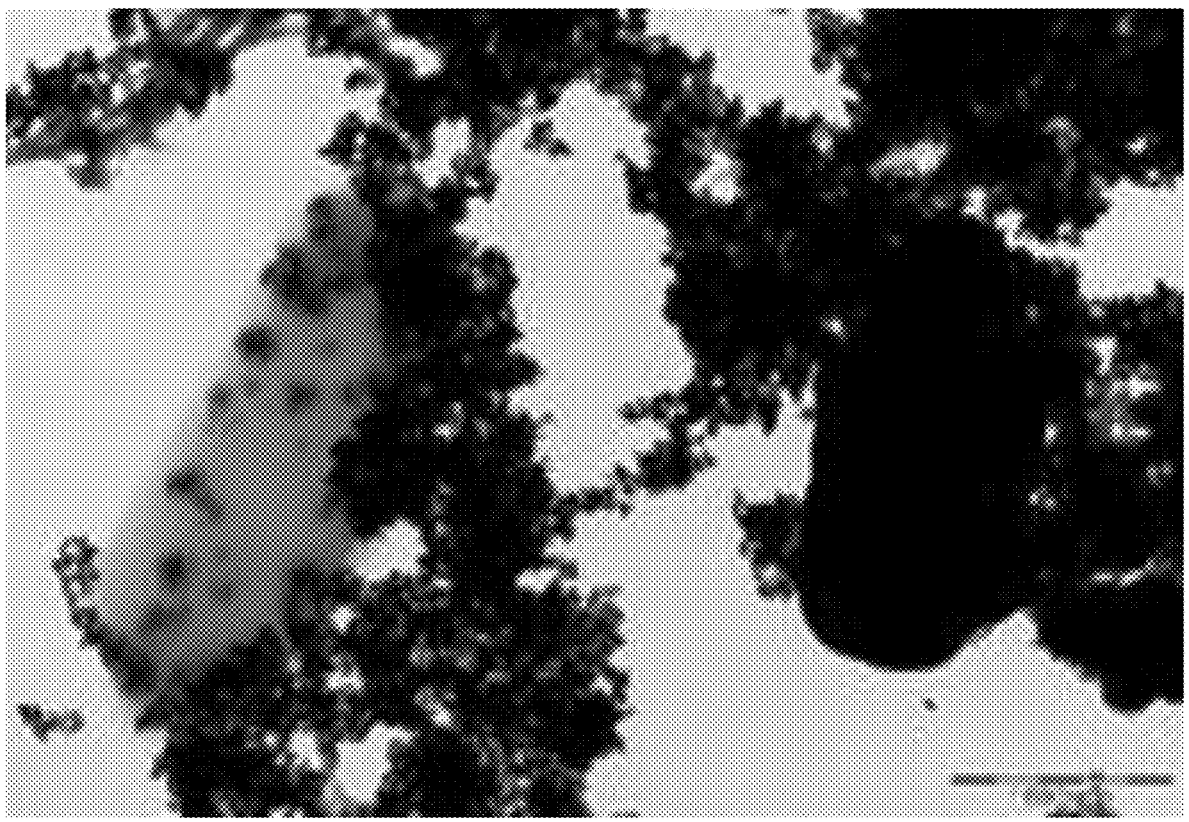
FIGS. 6A-6F depict effects of $C_1$ZNPS on resistant *E. coli* BAA-2471 and *E. faecium* 1449 alone and co-cultured after 16 hours exposure.
Figure 6B:
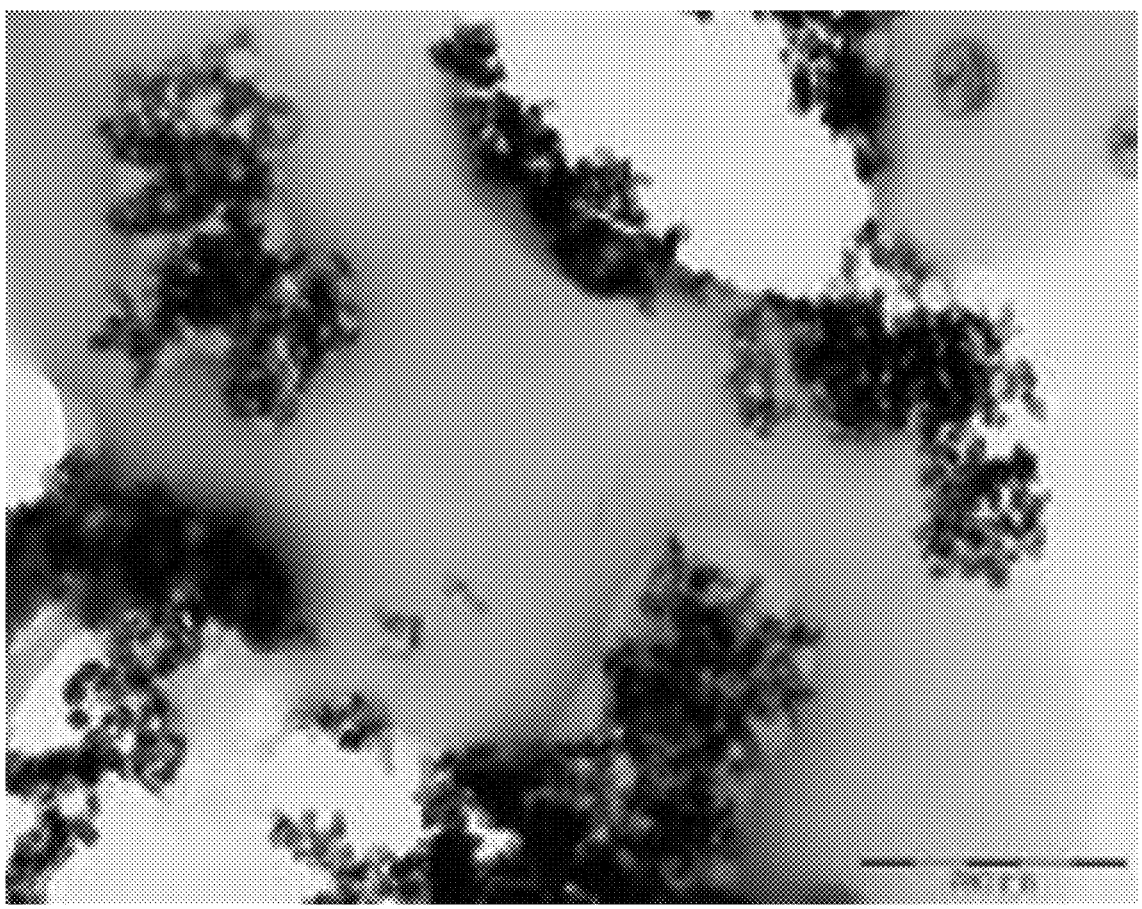
Figure 6C:
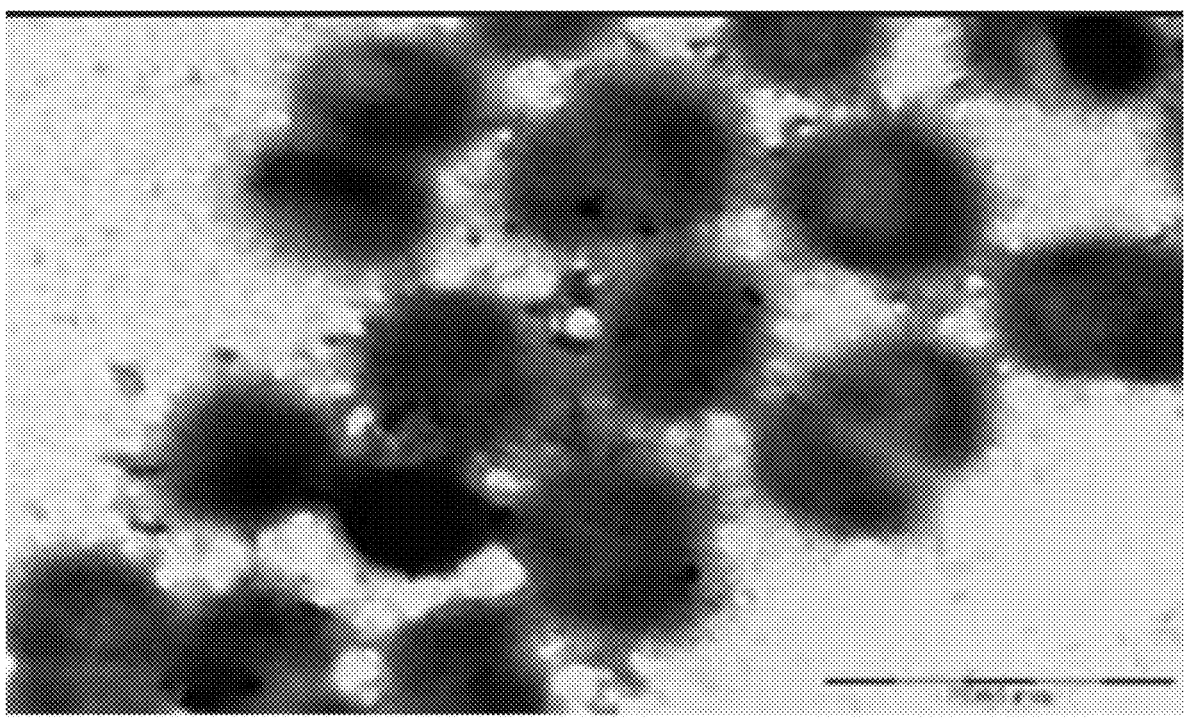
Figure 6D:
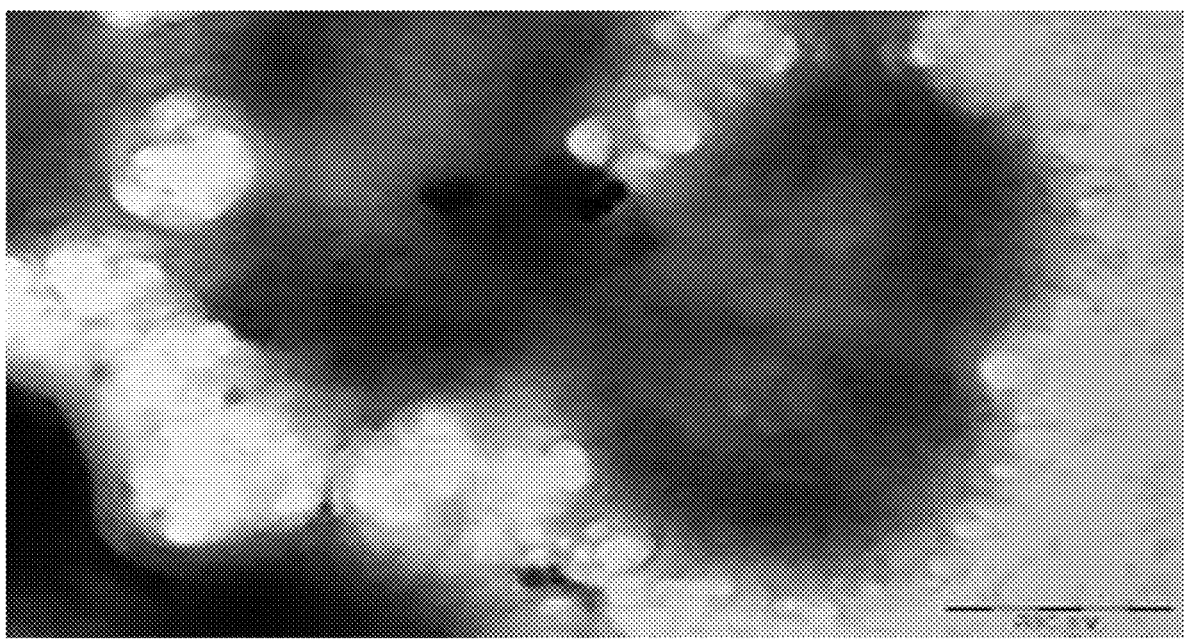
Figure 6E:
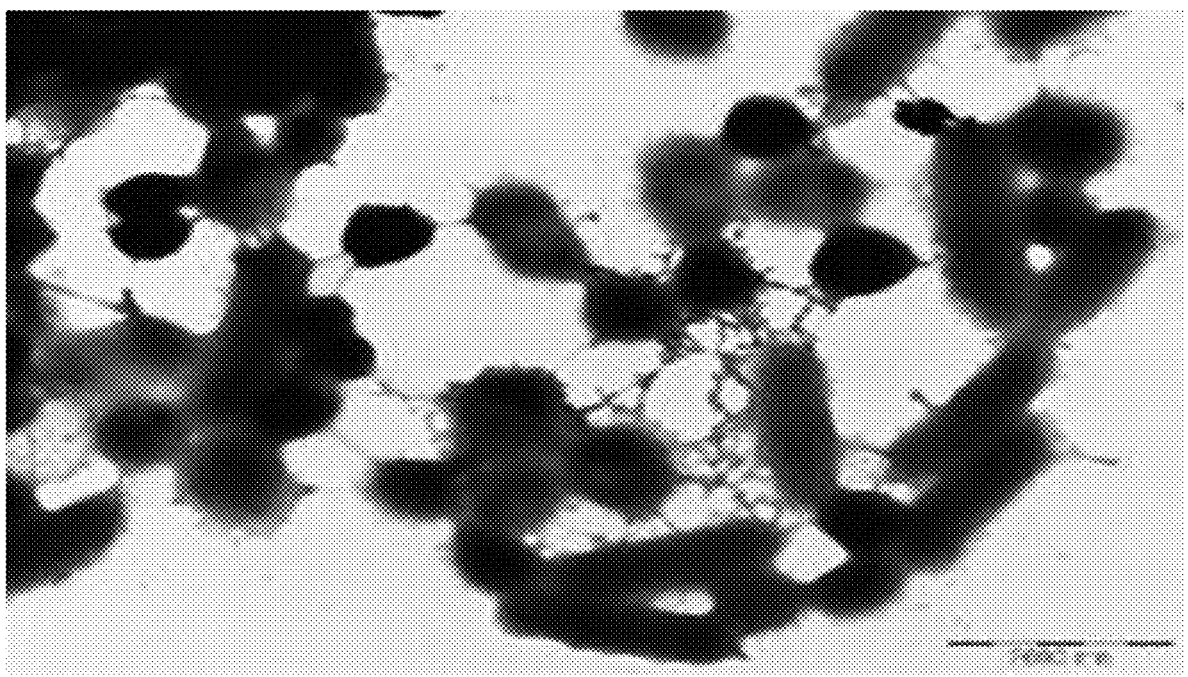
Figure 6F:
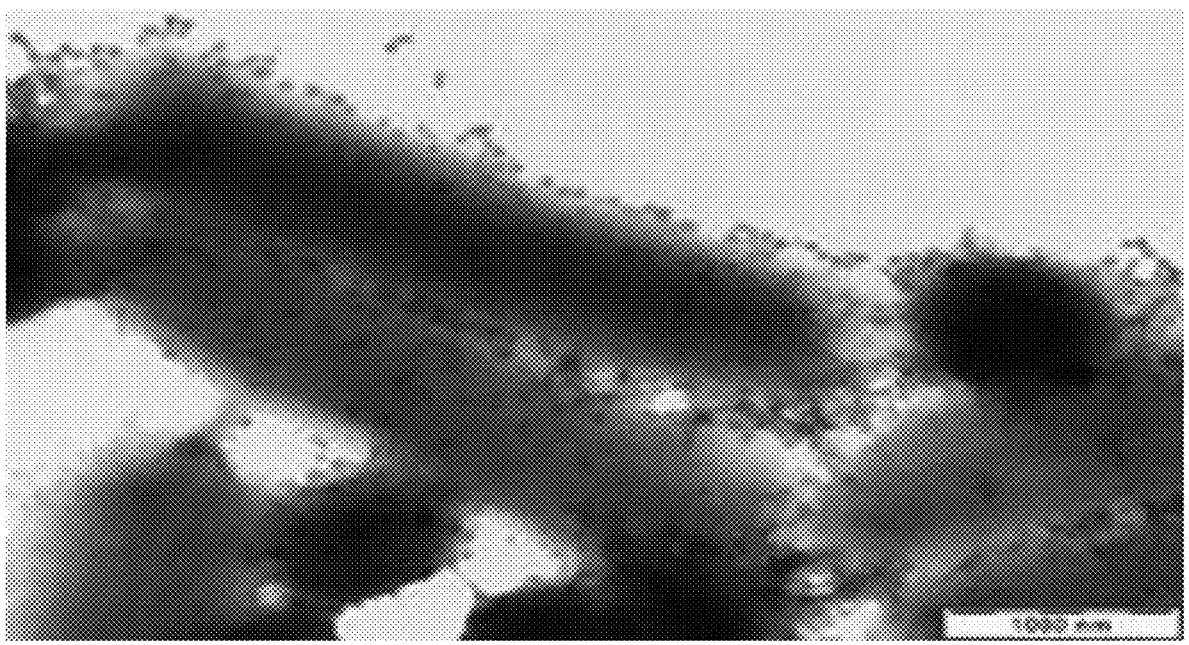

The antimicrobial efficacies of chitosan tested after 24 hours incubation at 37° C. are shown in Table 4. The chitosan 1 and 2 was not effective against both E. faecium culture and the co-culture, as well as against the WT cultures. However, chitosan 1 and 2 showed a significant inhibitory antimicrobial ability (0.0488 mg/mL) against multidrug resistant E. coli BAA-2471 culture, compared to non-effective against WT E. coli MCC 13 culture (FIG. 4). The MIC values of ZnO tested after 24 hours incubation at 37° C. are shown in Table 4. ZnO exhibited varying MICs against different cultures. According to the results, ZnO was more effective against WT E. coli MCC 13 (7.292 mg/mL) and WT E. faecium ATCC 35667 (0.391 mg/mL) than against resistant E. coli BAA-2471 (13.54167 mg/mL) and E. faecium 1449 (3.125 mg/mL), respectively. However, ZnO showed a slightly lower MIC of 5.208 mg/mL against resistant co-culture than the WT co-culture, with a MIC of 6.25 mg/mL (FIGS. 5A-5B).

TABLE 4

MIC values of Chitosan and ZnO against E. faecium and E. coli.

| | Strains of MRFs and Wild Type Counterparts | | | | | |
|---|---|---|---|---|---|---|
| Antimicrobials | E. coli BAA-2471 | E. coli MCC 13 (WT) | E. faecium 1449 | E. faecium ATCC 35667 (WT) | Co-culture of BAA-2471 and 1449 | Co-culture of MCC 13 and ATCC 35667 (WT) |
| | | | MIC: mg/mL | | | |
| Chitosan 1 (3 kDA) | <0.0488 | Not detected (>50) | Not detected (>50) | Not detected (>50) | Not detected (>50) | Not detected (>50) |
| Chitosan 2 (50 kDA) | 0.04883 | Not detected (>50) | Not detected (>50) | Not detected (>50) | Not detected (>50) | Not detected (>50) |
| ZnO | 13.54167 | 7.292 | 3.125 | 0.391 | 5.208 | 6.25 |

TABLE 4-continued

MIC values of Chitosan and ZnO against E. faecium and E. coli.

Strains of MRFs and Wild Type Counterparts

| Antimicrobials | E. coli BAA-2471 | E. coli MCC 13 (WT) | E. faecium 1449 MIC: mg/mL | E. faecium ATCC 35667 (WT) | Co-culture of BAA-2471 and 1449 | Co-culture of MCC 13 and ATCC 35667 (WT) |
|---|---|---|---|---|---|---|
| $C_1$ZNPS | <0.0488 | 2.604 | 1.563 | 3.125 | 0.781 | 2.083 |
| $C_2$ZNPS | <0.0488 | 2.083 | 1.042 | 2.604 | 1.302 | 3.125 |

The antimicrobial efficacies of synergism of chitosan and ZnO tested after 24 and 48 hours incubation at 37° C. are shown in Table 4. Both $C_1$ZNPs and $C_2$ZNPs presented markedly higher antimicrobial efficacy against resistant co-cultures than against WT co-cultures with a minimal average MIC of 0.781 mg/mL compared to 2.083 mg/mL, respectively. Furthermore, the effectiveness of the CZNPs complex was closely related to the molecular weight of chitosan. Indeed, the MIC values of CiZNPs against resistant E. coli BAA-2471, E. faecium 1449 and co-culture were 0.0488, 1.563 and 0.781 mg/mL, respectively. However, the MIC values of $C_2$ZNPs against resistant E. coli BAA-2471, E. faecium 1449 and co-culture were 0.0488, 1.042 and 1.302 mg/mL, respectively. Interestingly, $C_1$ZNPs with low MW (3 KDa) were significantly more effective than $C_2$ZNPs with high MW (50 KDa) against resistant co-culture. The MW was an important factor of NPs to impact the antimicrobial efficacy against bacteria cultures (FIGS. 6A-6F).

The antimicrobial efficacies of chitosan tested after 24 hours incubation at 37° C. are shown in Table 4. Chitosan 1 and 2 was not effective against both E. faecium culture and the co-culture as well as their WT cultures. However, chitosan 1 and 2 showed a significantly inhibitory antimicrobial ability (0.0488 mg/mL) against multidrug resistant E. coli BAA-2471 culture compare to non-effective against WT E. coli MCC 13 culture.

MIC values of the antimicrobials tested after 24 hours incubation at 37° C. are shown in Table 4. Zinc oxide and chitosan were tested alone and in equal combined level (1:1) against separate cultures and co-cultures of E. coli strain ATCC BAA-2471 and E. faecium strain 1449. Chitosan 1, and 2, which vary in molecular weights (3 and 50 kDa, respectively), were ineffective at low concentrations (<5%) against either strains of bacteria, as well as against the co-culture.

Zinc oxide only had relative effectiveness against E. faecium at a concentration of 3.125 mg/mL. Zinc oxide effectiveness at low concentrations against E. coli or against the co-culture was not detectable. The values denoted for combinatory antimicrobials are of total antimicrobial and therefore the concentration of each antimicrobial in these trials are half of the total concentration of antimicrobials. Detectable MICs were observed for the combination of antimicrobials against both separate cultures and the co-cultures. The $C_2$ZNPs were effective against E. coli and E. faecium alone with an MIC of 0.024 mg/mL and 12.5 mg/mL, respectively.

These trials give evidence for a synergistic property between the two antimicrobials (chitosan and ZnO) as trials showed effective inhibition of E. coli, E. faecium, and the co-culture as compared to the trials using just one antimicrobial, which were not detected (>5%). The MIC of $C_1$ ZNP against E. faecium was one-fourth of the MIC of zinc oxide against E. faecium. The MIC of the combined antimicrobial $C_1$ZNPs and $C_2$ZNPs in the co-culture was twice that of the MIC needed against the separate cultures. These values give evidence that these MRF strains increase their resistance to combined chitosan and ZnO when in the same culture. This gives evidence that the molecular weight of chitosan can greatly alter the effectiveness of the antimicrobial.

Considering the foregoing results, this study assessed the potential for remediation of multi-drug resistant bacteria of two different nanoparticles—chitosan and the ZnO. Although both have been evaluated previously either individually or in combination for their antibacterial properties, hitherto neither of these have been examined for potential for remediation of the multi-drug resistant bacteria.

Since the association between the molecular weight of chitosan and its antibacterial property has been controversial and this has not been studied for MRF and VRE strains, investigations were initiated using two different chitosan nanoparticles, one oligomeric chitosan (3 kDA) nanoparticles and a high molecular weight (50 kDA) chitosan. Chitosan presents distinct mechanisms according to whether a bacterium is gram-positive or gram-negative; in previous studies, electron micrographs for S. aureus and E. coli interacting with chitosan show how the cell membrane of S. aureus was weakened or even broken, while the cytoplasm of E. coli was concentrated and the interstice of the cell were clearly enlarged [Eisenstein B I, Jones G W, (1988) The spectrum of infections and pathogenic mechanisms of Escherichia coli. Adv Intern Med 33: 231-252], which provides ample evidence to suggest two main antibacterial mechanisms performed by chitosan.

For gram-positive bacteria, chitosan forms a polymer membrane around the cell's surface preventing any nutrients from entering while for gram-negative bacteria, chitosan with lower molecular weight entered the cell through pervasion. Chitosan seems to work more efficiently against gram-negative bacteria due to how its positively-charged structure adsorbs the electronegative substance in the cell and flocculate it to disturb the physiological activities of the bacteria and inhibit it.

However, chitosan is naturally a large molecule, and as such, the use of chitosan oligomers presents a stronger choice if the molecules would be combined with another compound for a synergistic effect. Although chitosan oligomers do not have the same level of antibacterial activity as chitosan, their smaller size allows for a lower molecular weight and the facilitation of penetrating the bacterial surface. The effect of this property is seen as chitosan oligomers seemed to have an increased antibacterial activity against gram-negative bacteria at lower molecular weight such as 1 kDa, where previous studies found that the growth of E. coli was reduced by 1 to 3 log cycles at a 1.0% concentration of chitosan oligomer with various degrees of polymerization. Moreover, the ZnO nanoparticle effect is more pronounced against gram-positive bacterial than against gram-negative bacterial strains [Orskov I, Orskov F (1985) *Escherichia coli* in extra-intestinal infections. J Hyg (Lond) 95: 551-575].

Gram-positive bacteria have a thick layer of peptidoglycan polymer that encircles the cell and a much thicker cell wall, while gram-negative have bacteria two thin cell membranes divided into an outer membrane and a plasma membrane. Therefore, they both require different agents against their different structures. Chitosan oligomers' polysaccharide structure not only contain transcellular properties to cross cellular membranes, they also contain mucoadhesive and bioadhesive properties that contribute to their absorption improving effects. The positively-charged chitosan does not only bind to negatively-charged oxides, it also can bind to different drugs or peptide hormones like calcitonin to deliver a specific dose effectively, partly due to its bioadhesive properties with gram-negative bacterial membranes or negative mucus in tissue membrane in the case of calcitonin delivery.

Since chitosan has the structural ability to bond to metal oxide compounds, such as the ionic ZnO, a possibility exists to develop an antimicrobial agent that can efficiently work against both types of bacteria by bonding these two compounds to create a synergistic combination that targets a broader range of bacteria found in food products without risking human health. The applicability of ZnO as an antimicrobial agent is due to its morphology that broadens the uses of it against various bacteria. The compound's structure allows for an easier biocompatibility over other metal oxides, solubility in alkaline medium, and the Zn—O terminated polar surfaces. Zinc oxide nanoparticles seem to inhibit or cause bacterial death more efficiently when they are smaller in size but higher in concentration. A smaller size at higher concentrations provides higher specific surface areas and facilitates the penetration of the antimicrobial agent into the bacterial membrane. Virtually every unique property of ZnO proves to be beneficial in regard to antibacterial activity. Although ZnO is usually insoluble in water due to its high polarity, it can be managed efficiently in an aqueous cell culture media, such as TSB. Zinc oxide possesses photo-oxidizing and photocatalysis impacts on chemical and biological species, which when combined with its bio-safe composition, provides a safe interaction on food products where they come in contact with bacteria to inhibit and/or kill it to prevent food-related diseases.

Additionally, this study adds a perspective on the increased effectiveness of chitosan by molecular weight when in the presence of ZnO. While the oligomer of chitosan (3 kDA) in literature shows the least potential as a possible effective antimicrobial, the effectiveness of chitosan oligomers against MRFs was substantially amplified by the addition of ZnO. The discrepancy between this data and the current literature may be due to the presence of ZnO along with the structural modifications of the chitosan oligomers used to generate optimal conditions.

Combination of chitosan oligomers with ZnO nanoparticles demonstrated synergistic effects in remediation of important food-borne bacteria including the resistant strains. Until now, there has been no quantitative data thus far on the precise concerted effect of these nanoparticles against multidrug resistant microbes. This experiment has demonstrated the effect against both multi-drug resistant gram-positive and gram-negative fecal bacteria while comparing the combinatory antimicrobial properties to the individual nanoparticles. The overall objective of this experiment was to ascertain the efficacy of CZNPs synergism on co-cultured MRF strains through validated MIC tests and TEM assays. A specific goal was to validate a nanotherapeutic agent to further in situ intervention.

This research study has demonstrated this success of CZNPs against both multi-drug resistant gram-positive and gram-negative fecal bacteria while comparing the combinatory antimicrobial properties to the individual nanoparticles. Synergism of CZNPs primarily $C_1ZNPs$ proved to be successfully suppressive to MRFs over WT strains. It is concluded that $C_1ZNPs$ has therapeutic potential to in situ intervention.

Experiment/Study 3 (Molecular Identification and Nanoremediation of Lytic Biofilm in Algal Systems using Untreated Wastewater)

Wastewater-algal biomass is a promising option for algae cultivation, which may be used for biofuel production. However, multidrug resistant biofilm constitutes a medium to potential infection in algal cultivation workers. An objective of the current study was to develop a comprehensive screening of the most prevalent bacterial consortia found in biofuel reactors and study the effectiveness of CZNPs against such harmful bacteria.

The synergistic application of chitosan oligomers with ZnO nanoparticles showed promise for a method that utilizes low molecular weight chitosan derivatives with the increased surface area of ZnO nanoparticles. The notable antimicrobial properties of ZnO are optimized by the use of chitosan oligomers that contain transcellular properties to cross cellular membranes and its structural ability to bond to metal oxide compounds. Chitosan's mucoadhesive and bioadhesive properties with Gram-negative bacteria present a favorable opportunity to transport CZNPs to lytic microbial groups found in algal wastewater systems such as *Pseudomonas aeruginosa*, and several *Bacillus* strains [Zhang, H. et al. Absorption-improving effects of chitosan oligomers based on their mucoadhesive properties: A comparative study on the oral and pulmonary delivery of calcitonin. Drug Deliv. 2014, 21(6), 397-500]. Together, chitosan and ZnO work synergistically to target both Gram-positive and Gram-negative bacteria, thus mimicking a broad-spectrum antibiotic.

Briefly, a series of algal strains, *Nannochloris oculata* and *Chlorella vulgaris* samples (n=30), were purchased from the University of Texas, and were used for both stock flask cultures and flat-panel vertical bioreactors. A number of media were used for isolation and differentiation of potential contaminants according to laboratory standards (CLSI). Conventional PCR amplification was performed followed by 16S rDNA sequencing to identify isolates at the species level. Nanotherapeutics involving a nanomicellar combination of natural chitosan and zinc oxide (CZNPs) were tested against the microbial lytic groups through MIC tests and TEM.

Results indicated the presence of *Pseudomonas aeruginosa, Bacillus pumilus/safensis, Cellulosimicrobium cellulans, Micrococcus luteus* and *Staphylococcus epidermidis* strains at a substantial level in the wastewater-fed algal reactors. TEM confirmed the effectiveness of CZNPs on the lytic group while the average MICs (mg/mL) detected for the strains—*Pseudomonas aeruginosa, Micrococcus luteus*, and *Bacillus pumilus*—were 0.417, 3.33, and 1.458, respectively. Conclusively, CZNP antimicrobials proved to be effective as inhibitory agents against currently identified lytic microbial group, did not impact algae cells, and shows promise for in situ interventions.

A. Materials and Methods i. Sample collection

A series of algal strains namely, *Nannochloris oculata* Droop UTEX LB 1998 and *Chlorella vulgaris* Beijerink UTEX 259 samples, were purchased from the Culture Collection of Algae at the University of Texas. The samples were used for both stock flask cultures and flat-panel vertical bioreactors in the biofuel lab at the Patel College of Global Sustainability at the University of South Florida, Tampa, Fla., USA.

ii. Differential/Selective Media Test

A number of selective and differential media such as tryptic soy agar (TSA), blood agar, starch agar, eosin-methylene blue (EMB) agar, MacConkey agar, salmonella-shigella (SS) agar, triple sugar iron (TSI) agar, xylose lysine deoxycholate (XLD) agar and mannitol salt agar (MSA) were used for isolation and differentiation of potentially harmful bacteria according to Clinical & Laboratory Standards Institute (CLSI) guidelines.

iii. PCR Assay and Gel Electrophoresis

DNA was extracted from isolated pure cultures using the QIAamp DNA Mini Kit (Qiagen, Valenica, Calif., USA) according to the manufacturer's instructions. The purity and yield of the extracted DNA was checked using the ND-1000 Nano-Drop spectrophotometer (Fisher Scientific, Pittsburgh, Pa., USA). Conventional PCR amplification targeting the 16S rRNA gene was performed using the following primer set: 8F: 5'-AGA GTT TGA TCC TGG CTC AG-3' (SEQ ID NO:1), 1492R: 5'-GGT TAC CTT GTT ACG ACT T-3' (SEQ ID NO:2). The PCR reaction was performed in a Mini-opticon with the following conditions: initial denaturation for 2 min at 94° C., 40 cycles of 1 min at 94° C. for denaturation, 1 min at 50° C. for annealing and 2 min at 72° C. for extension, a final extension of 4 min at 72° C., then 4° C. for holding the PCR products. 5 mL of amplified products along with 2 mL of 6× loading dye were stained with ethidium bromide and electrophoresed in a 2.0% agarose gel at 120 V for 15 min along with a 100 bp Ladder to verify product size. PCR products were further identified using 16S rRNA analysis (Table 5).

TABLE 5

Isolate identification at the genus-level by 16s rRNA sequencing.

| Tube ID | Bacterial isolate |
|---|---|
| A | *Pseudomonas aeruginosa* |
| B | *Pseudomonas aeruginosa* |
| C | *Pseudomonas aeruginosa* |
| D | *Pseudomonas aeruginosa* |
| E | *Pseudomonas aeruginosa* |
| F | *Pseudomonas aeruginosa* |
| Q | *Pseudomonas aeruginosa* |
| R2 | *Bacillus pumilus/Bacillus safensis* |
| Pond 1 | *Aeromonas* sp. |
| Pond 2 | *Pseudomonas aeruginosa* |
| Pond 3 | *Pseudomonas aeruginosa* |
| Pond 4 | *Staphylococcus warneri/Staphylococcus pasteuri* |
| Well 1 | *Brevi bacillus* sp. |
| Well 2 | *Bacillus* sp. |
| H | *Cellulosimicrobiumcellulans* |
| M | *Micrococcus luteus* |
| S | *Staphylococcus epidermis* | iv. Preparation and Characterization of CZNPs

Medium molecular weight of chitosan powder (MW: 10 kDa; surface area: 4.56-0.74 m2/gL; surface porosity 89.3%; zeta potential: 36 mV-40 mV; acidity/basicity 6.2-7.0) along with hydrophobic ZnO powder (surface area: 54 m$^2$/g (MW: 20 nm); composition: 80.34% zinc and 19.6% oxygen; zeta potential: 9.5 mV-10 mV; acidity/basicity 6.5-7.0; crystallinity: Zincite, hexagonal wurtzite) were purchased from Sigma Aldrich, St. Louis, Mo. The degree of viscosity of chitosan were approximately 90% associated with hydrated and anhydrous crystallinity. The stock solution was prepared by dissolving spontaneously both agglomerate nanoparticle in 1% (v/v) of acetic acid 2.0 mg/mL and was adjusted pH using (NaOH) and stored at room temperature that should not exceed 25° C. The synthesis and purification of the CZNPs were performed based on Premanathan et al. [Premanathan, M. et al. Selective toxicity of ZnO nanoparticles toward Gram-positive bacteria and cancer cells by apoptosis through lipid peroxidation. Nanomedicine 2011, 7, 184-192] and Zhang et al. [Zhang, H. et al. Absorption-improving effects of chitosan oligomers based on their mucoadhesive properties: A comparative study on the oral and pulmonary delivery of calcitonin. Drug Deliv. 2014, 21(6), 397-500] protocols with some additional modifications. It includes the optimization of the core shell structure by designing a hydrophobic interior comprising ZnO with imaging moiety surrounded by an anionic functionalized lipid micellar (i.e., DOPA (1,2-dioleoyl-sn-glycero-3-phosphate); Avanti Polar lipid, Inc.) and chitosan coat shell.

v. MIC Assays

The lytic bacterial strains of *Pseudomonas aeruginosa*, *Bacillus* spp., and *Micrococcus luteus* cultured overnight were diluted 1 in 1,000 in fresh TSB) broth (Sigma, St. Louis, Mo., USA). A sterile 96-well microtiter plate was labeled. To all the categorized wells was added 50 mL of TSB. Each well was loaded with 50 mL of the bacterial suspension (5×108 CFU/mL) and screened against 1.0% CZNPs by 1:2 dilution to equal a total volume of 100 mL in each of the wells according to NCCLS. All tests were performed in triplicate with identical results. The plates were incubated at 37° C. overnight and the MICS were determined after 24 h by visual determination of the minimum level of antimicrobial to inhibit growth. Inhibition of growth was determined by lack of turbidity in the wells.

vi. Microscopic Characterization using TEM

Aliquots of bacteria in growth media were initially fixed in equal volume of 2% osmium tetroxide in distilled water for 1 h at 4° C. Following fixation, the bacteria were rinsed in distilled water and pelleted at 5000 RPM for 10 min. This rinse step was repeated three times. A proper dilution of bacteria was obtained to yield approximately 2000-3000 bacteria per drop, and one drop of a sample was applied to a carbon-formvar coated copper grid. The grid was allowed to air dry. This procedure was repeated for each sample. Once dry, the grids were observed and photographed in an FEI Morgagni transmission electron microscope (FEI Corp., Hillsboro, Oreg., USA).

B. Results

Figure 7:
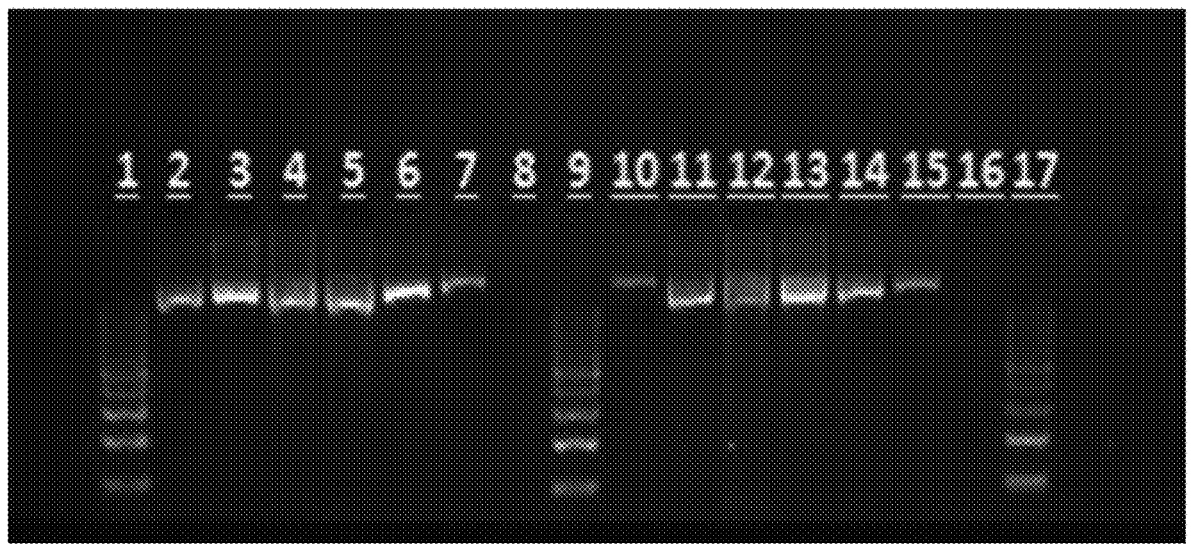
FIG. 7 depicts [16s rDNA]-Digested Waste (A-E) 11-10-2015 J. S.
Figure 8A:
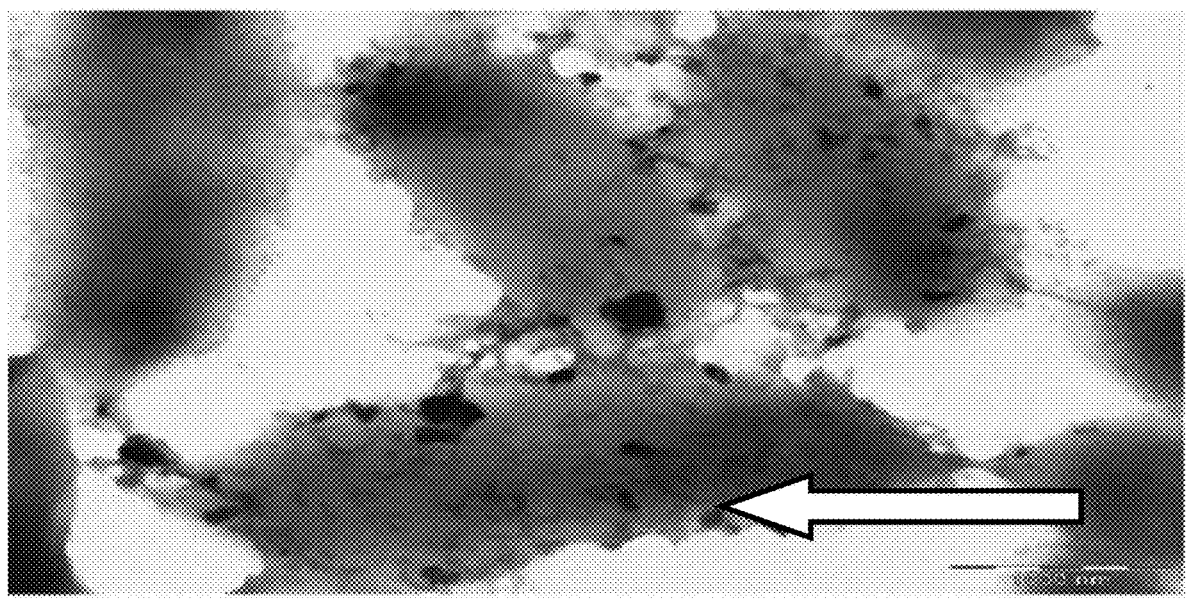
FIGS. 8A-8F are TEM images after 24 h exposure of nanoparticles against multidrug resistant bacteria and algae.
Figure 8B:
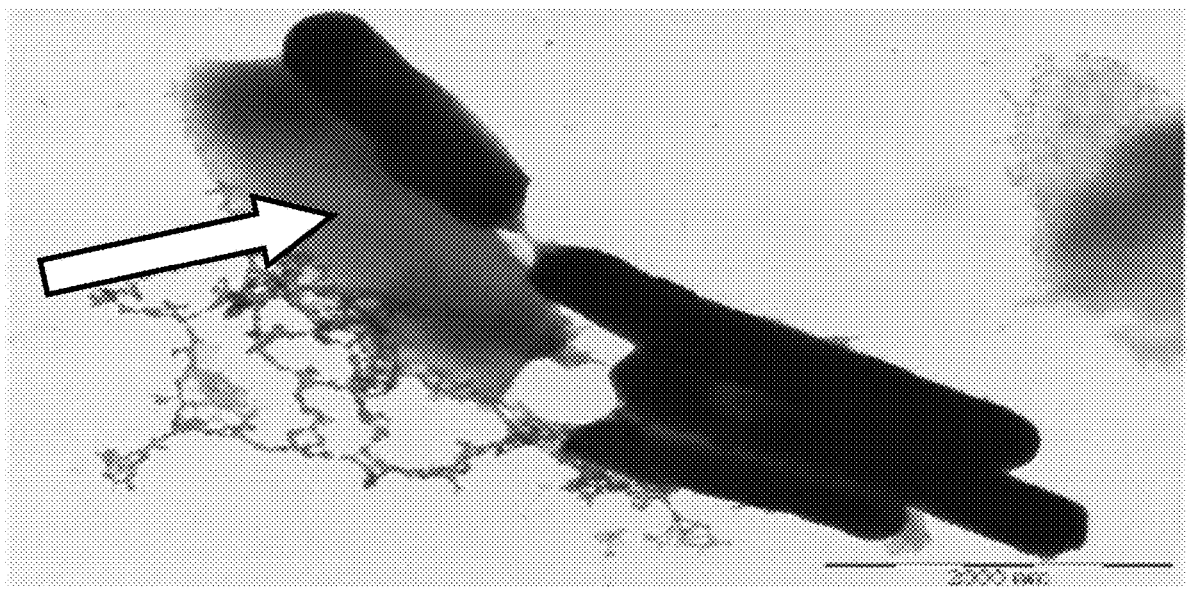
Figure 8C:
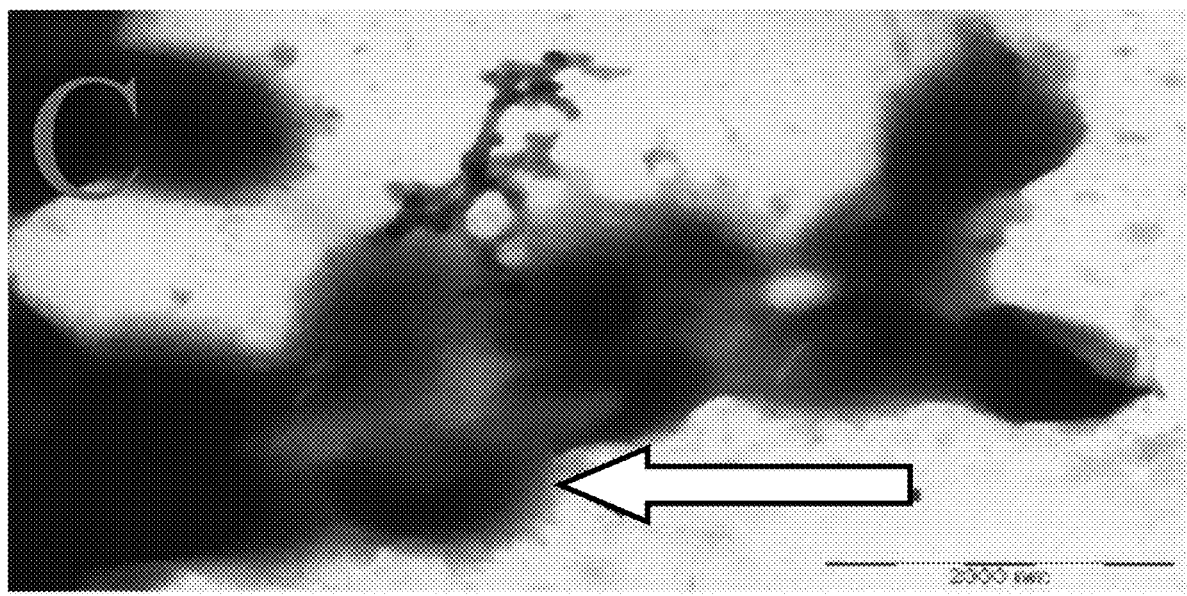
Figure 8D:
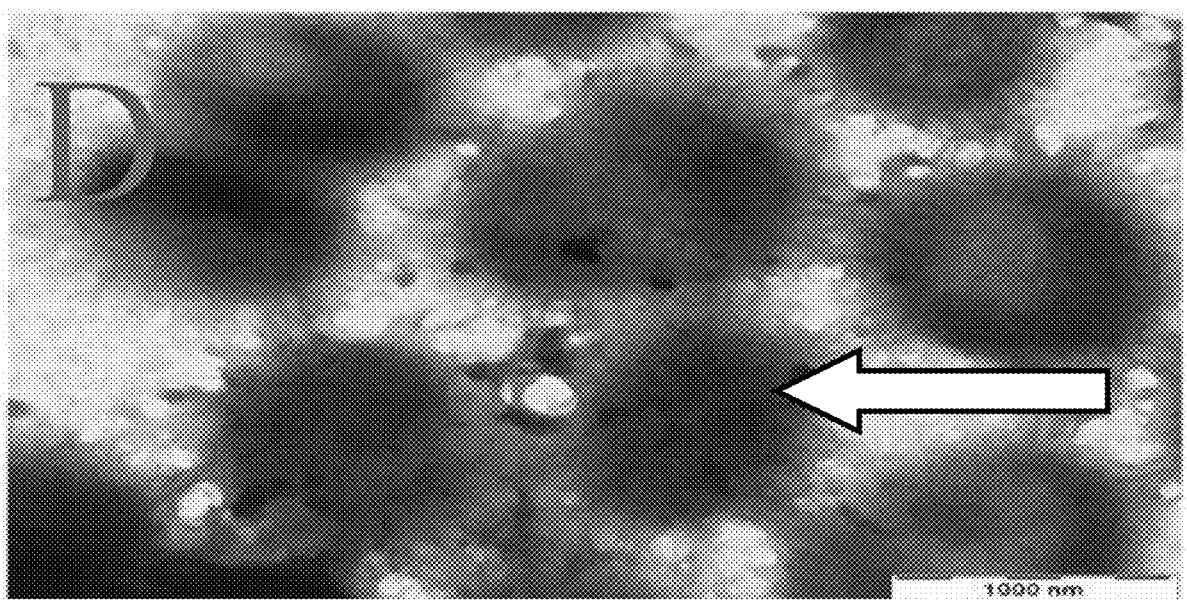
Figure 8E:
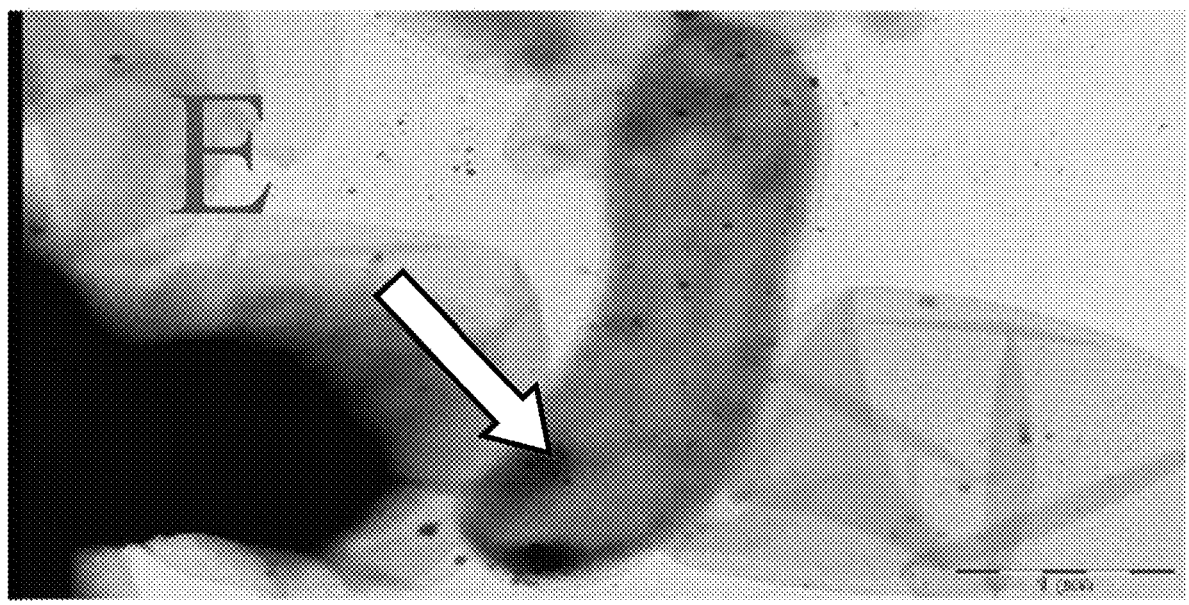
Figure 8F:
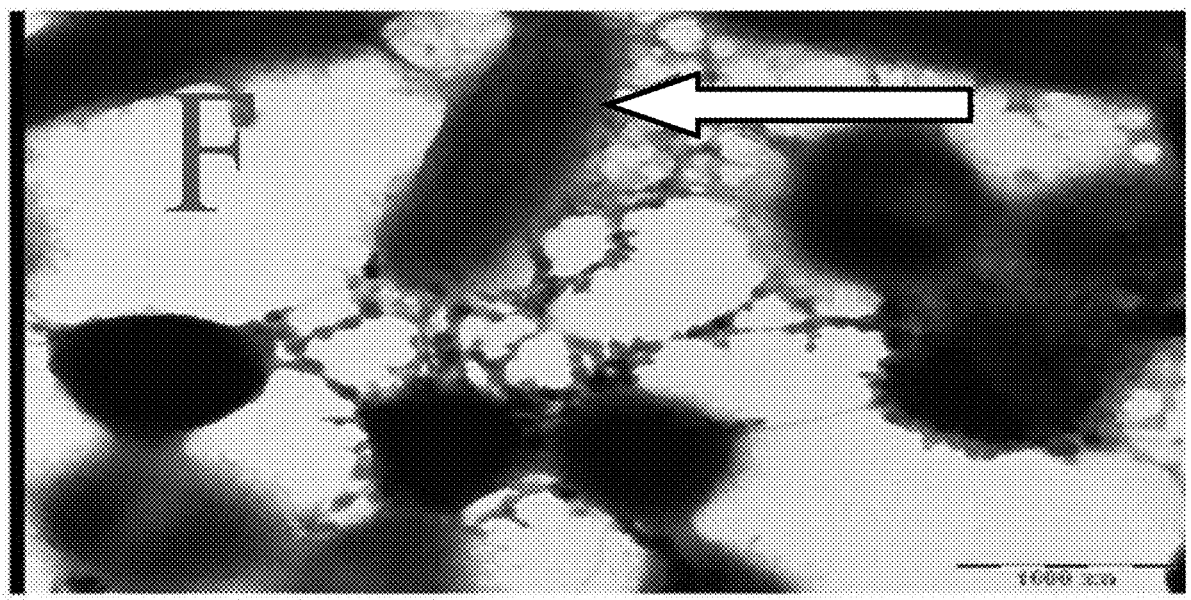
Figure 8G:
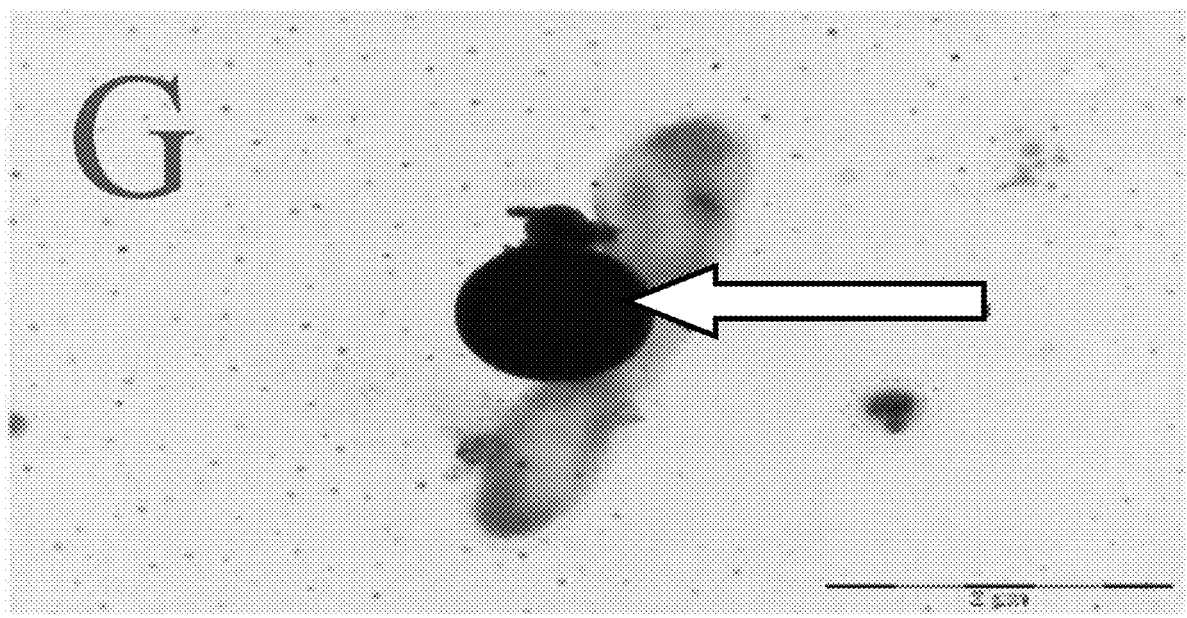
FIG. 8G depicts a single algae cell in front of a dying lysed Gram-negative bacteria. The high electron density of the spherical species when compared to the Gram-negative bacteria indicate the cell is largely unaffected. Small scattered electron densities show the CZNPs outside of the meshing.

The preliminary findings elucidated a wide range of microbial contaminants of approximately 20 microorganisms including fungi along with numerous rod-shaped Gram-positive and Gram-negative bacteria. The presence of *Pseudomonas* as evidenced by colorless colonies on EMB and MacConkey agar was particularly interesting for its previously documented lytic effects on algal growth. The colorless and yellow colonies presented in MSA media suggested the appearance of *Staphylococcus epidermidis* and *Micrococcus luteus*, respectively [Gumbo, J. R. et al. The isolation and identification of predatory bacteria from a Microcystis algal Bloom. Afr. J. Biotechnol. 2010, 9, 663-671]. Gel electrophoresis of amplified PCR products demonstrated distinct bands (FIG. 7). The absence of a band in the negative control indicates no degradation of target DNA and the absence of non-specific amplicons. The presence of strains presumptively identified using culture-based methods and some others that could not be identified was confirmed at the genus level by 16S rRNA sequencing (see Table 5). Many isolates were also identified at species level by further 16S rRNA sequencing as follows: *Pseudomonas aeruginosa, Bacillus pumilus/safensis, Cellulosimicrobium cellulans, Micrococcus luteus*, and *Staphylococcus epidermidis*.

i. Microscopic Characterization using TEM

Identified strains of *Pseudomonas, Micrococcus*, and *Bacillus* were prepared for TEM to observe reaction against synergistic antimicrobial attack of chitosan (10 kDa) oligomers and ZnO nanoparticles after exposure for 24 h. The microscopy performed on the lytic bacteria revealed protrusions of microbial cell membranes with clear alterations caused by CZNPs in the bacteria's cell wall structure, cellular shape, and electron density compared to microbial control cells (FIGS. 8A-8G). Images for each bacterial group were collected to demonstrate the lytic effect CZNPs have on them, as can be seen in FIGS. 8A-8G.

ii. MIC

TEM confirmed the effectiveness of CZNPs on lytic groups *Pseudomonas, Bacillus*, and *Micrococcus luteus* (FIGS. 8A-8G) after 24 h of exposure. Cell death and lysis is observed through the contrast of low electron density in the bacterial cell as opposed to the high electron density of the invading nanoparticles. The antimicrobial effectiveness of chitosan and ZnO, separate and combined, after 24 h incubation at 37° C. are shown in Table 6. Every bacterial lytic group was exposed to an antimicrobial or combination of antimicrobials in triplicate, and results shown are average between the trials. Antimicrobial susceptibility of the lytic groups against the individual application of chitosan 10 kDa provided similar inhibitory concentrations for *Pseudomonas* (2.083 mg/mL), *Micrococcus luteus* (2.083 mg/mL), and *Bacillus* (1.875 mg/mL).

Zinc oxide was not effective against *Pseudomonas*, having an MIC test result of 8.333 mg/mL, in contrast to its synergistic combination with chitosan that exhibited significant antimicrobial activity against the same bacteria with an MIC result of 0.417 mg/mL. Moreover, ZnO nanoparticles presented significant antimicrobial activity against Gram-positive *Micrococcus* (0.417 mg/mL) shown in Table 6. The MIC results demonstrated synergistic antimicrobial effect against all groups, as (1) the adhesive properties of chitosan with Gram-negative bacteria (*Pseudomonas*) enhance the delivery of nanoparticles across cellular membranes and (2) chitosan has the ability to polymerize around the surface of Gram-positive bacteria to inhibit nutrient intake. Furthermore, ZnO nanoparticle effects are more pronounced against Gram-positive bacteria than Gram-negative bacterial strains, increasing the range of antimicrobial capacity of CZNPs. All MIC test results using chitosan-ZnO against *Pseudomonas* (0.417 mg/mL), *Micrococcus luteus* (3.333 mg/mL), and *Bacillus* (1.458 mg/mL) proved efficient when suspended in TSB.

TABLE 6

MIC values of CZNPs on lytic bacterial consortia.

| Antimicrobials | MIC presented in mg/mL | | |
|---|---|---|---|
| | Pseudomonas | Micrococcus luteus | Bacillus |
| Chitosan 1 (10 kDA) | 2.083 | 2.083 | 1.875 |
| Zinc Oxide | 8.333 | 0.417 | 1.250 |
| Zinc Oxide + Chitosan 1 | 0.417 | 3.333 | 1.458 |

In conclusion, the current study found the presence of the lytic genera of *Pseudomonas, Micrococcus, Staphylococcus*, and *Bacillus* at a substantial level in the wastewater-fed algal reactors, for which the CZNPs complex was a promising nano-remedy that can be used in concentrations without affecting algae cells.

Example

Figure 9:
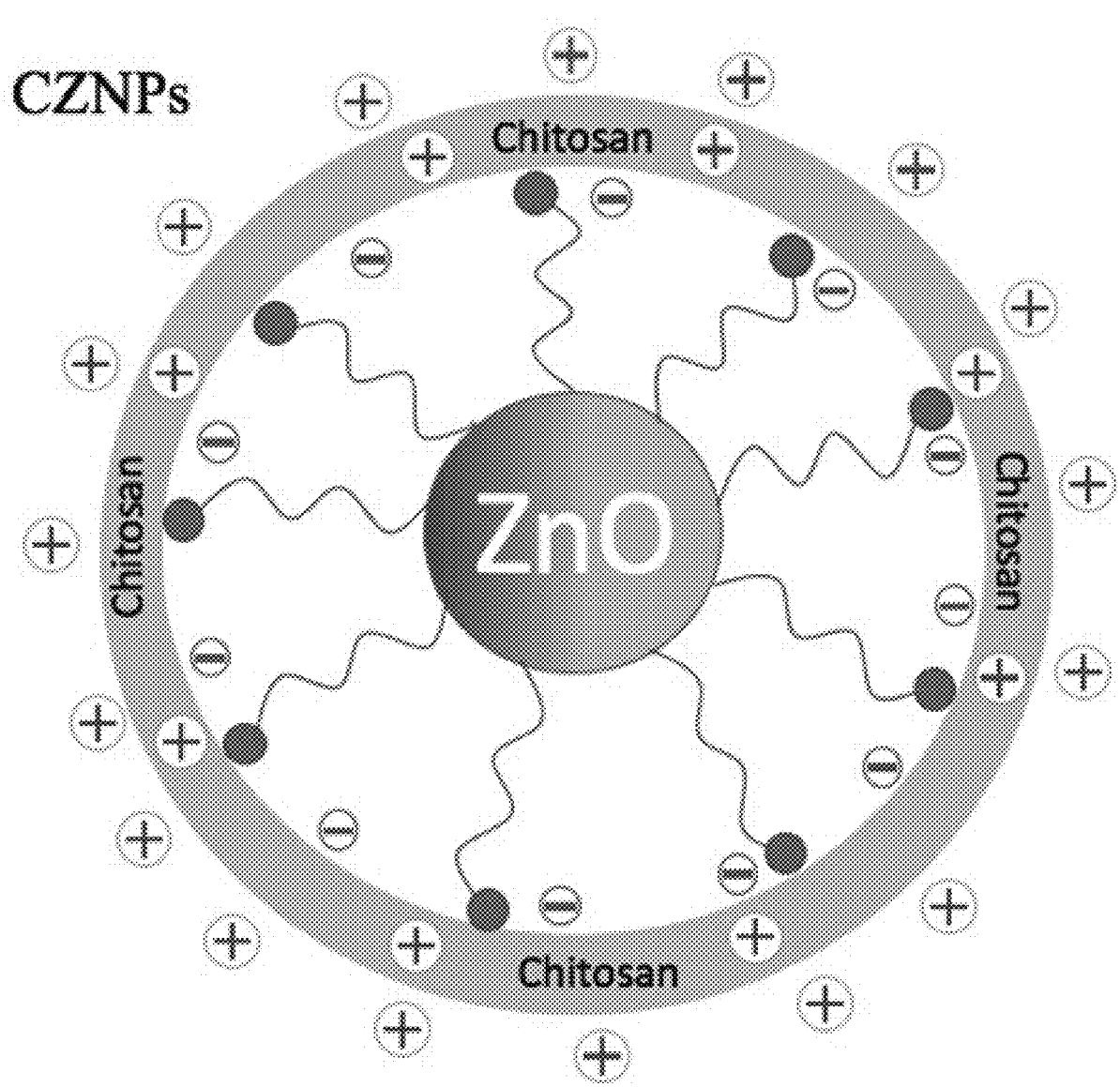
FIG. 9 depicts the structure of synthesized CZNPs, according to an embodiment of the current invention.
Figure 10:
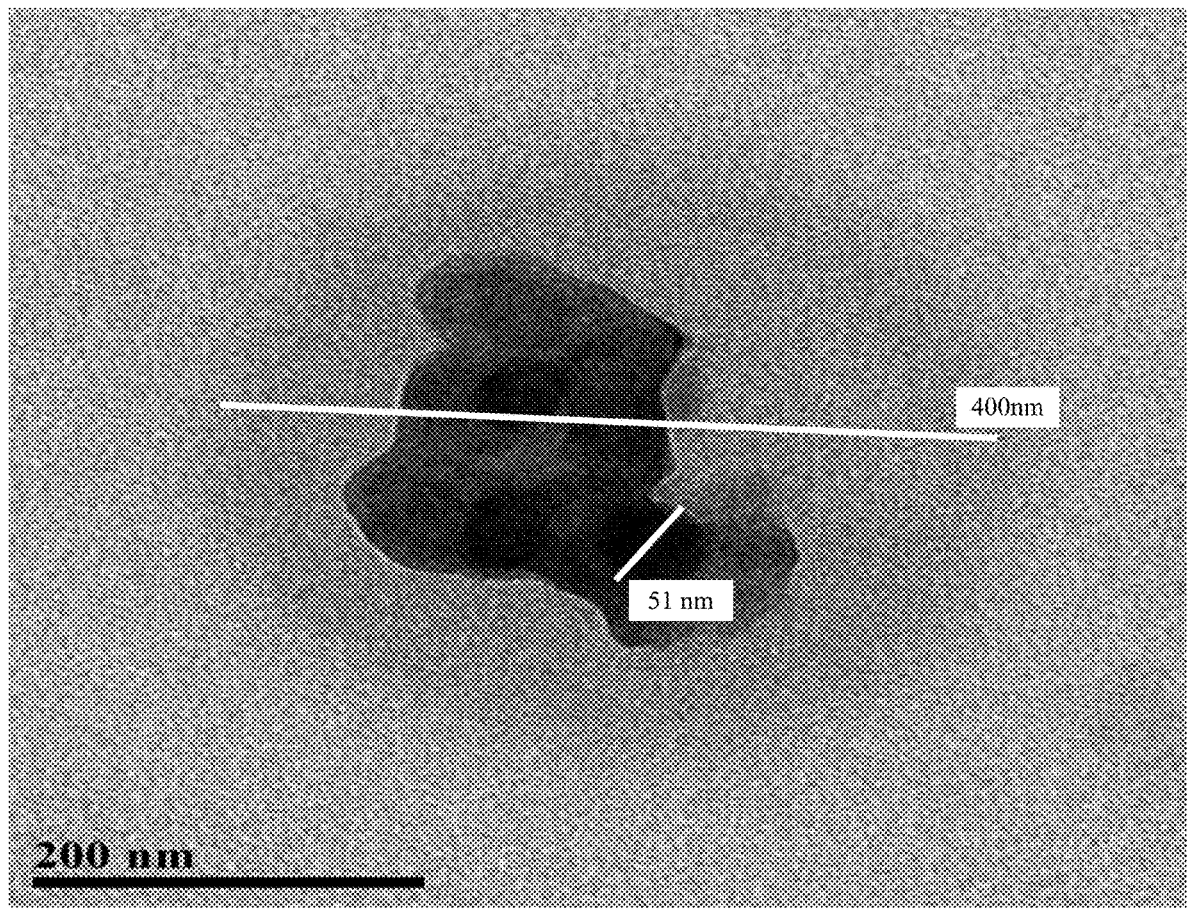
FIG. 10 is an SEM image of CZNPs structure, according to an embodiment of the current invention.
Figure 11:
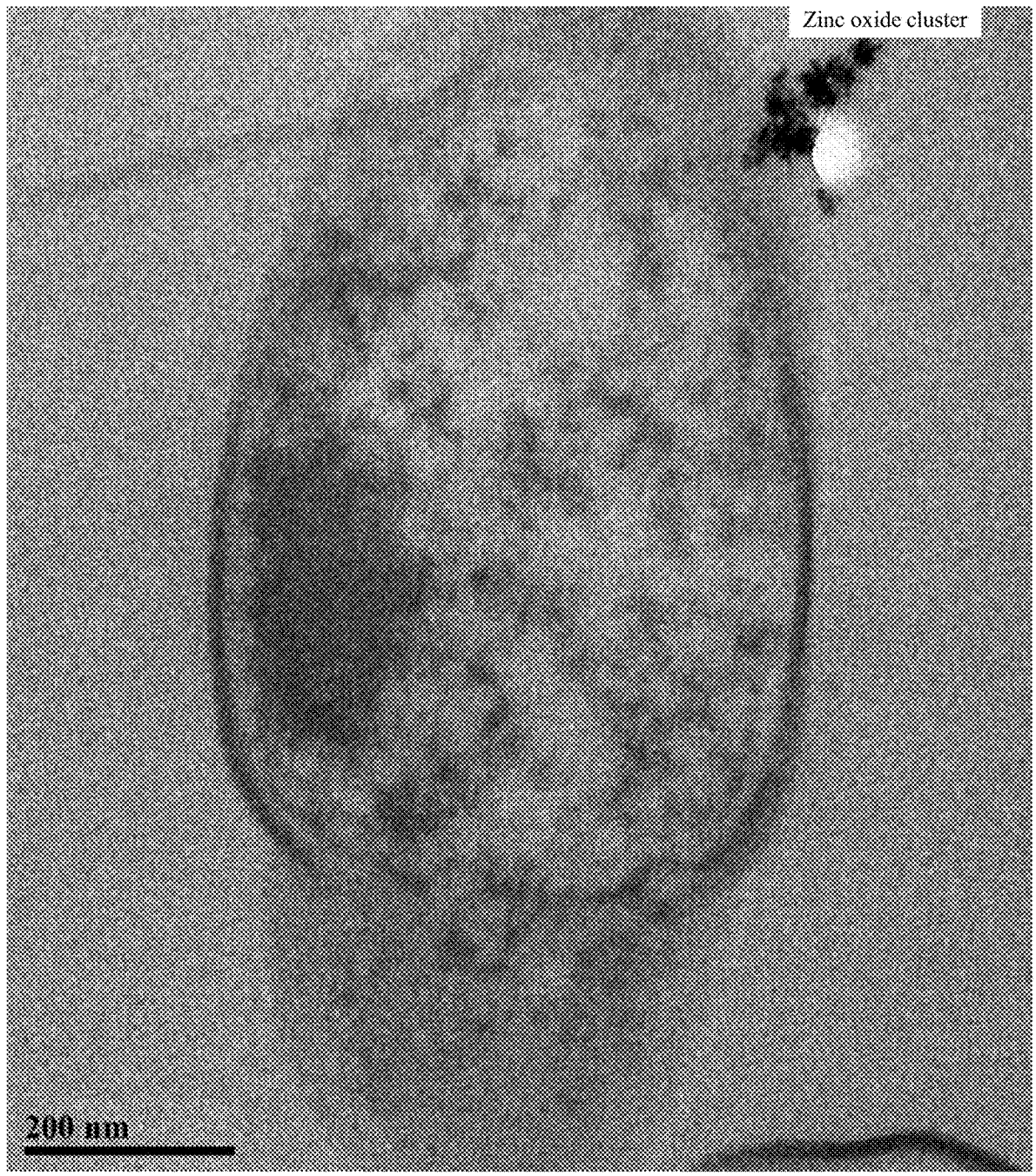
FIG. 11 depicts CZNPs size in comparison to *E. coli* BAA-2471.

An exemplary structure of the nanomicellar CZNP can be seen in FIG. 9. The ZnO particles comprise the center of the composite. An anionic lipid micellar shell surrounds the ZnO particles. The cationic chitosan coats the outside of the nanocomposite, covering the lipid micellar shell. Viewed under a scanning electron microscope, FIG. 10 is an image of the CZNPs structure. ZnO particles are seen as dense black spheres, surrounded by a dark gray lipid micellar shell. The chitosan coating is seen as a faint grey exterior. FIG. 11 specifically illustrates the size of the CZNPs compared to the bacteria on which they are to act.

Figures 12A, 12B:
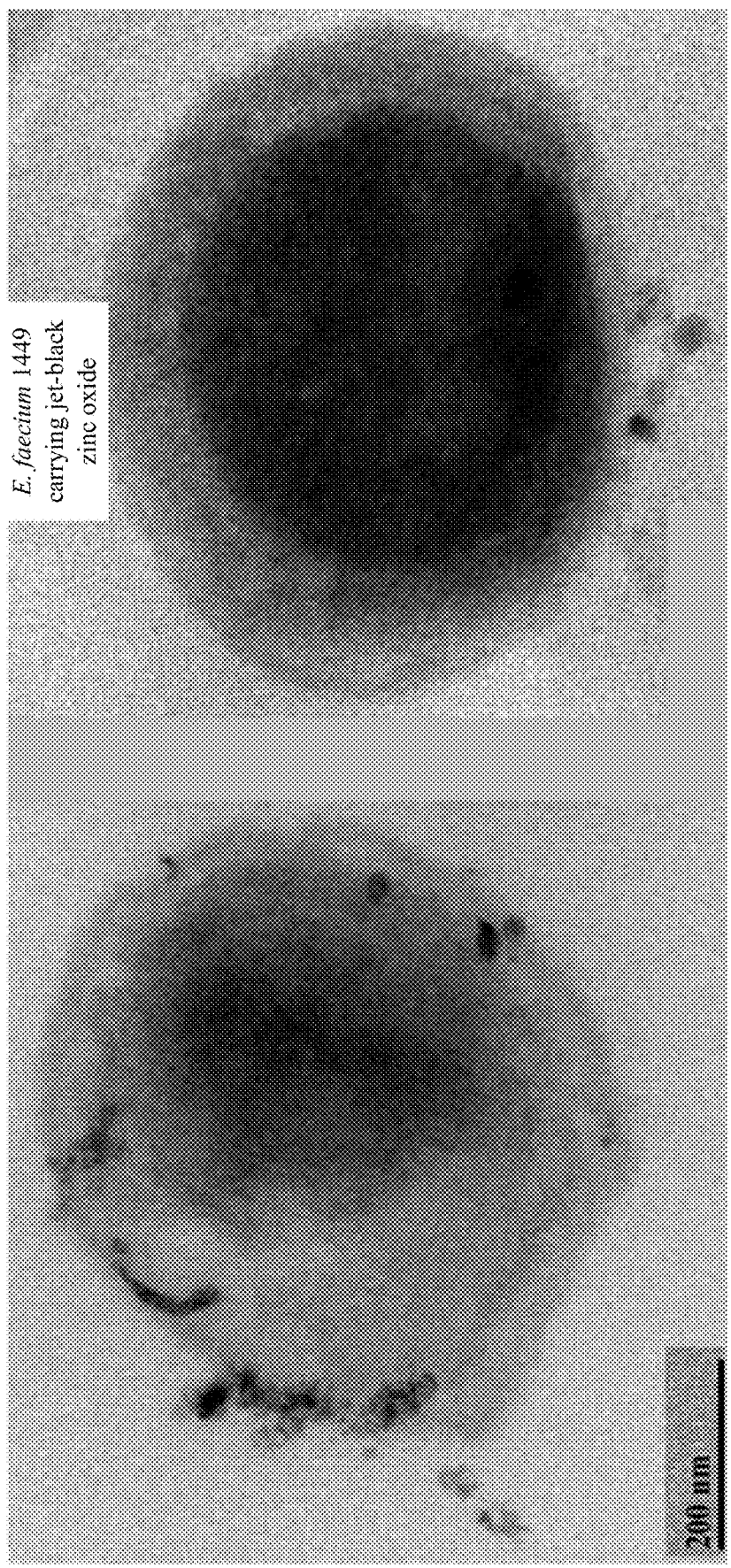
FIG. 12A is an SEM image of CZNP entering Gram-positive *E. faecium* 1449 bacterial cell.
FIG. 12B is an SEM image of ZnO filling the interior of the Gram-positive *E. faecium* 1449 bacterial cell.

Now referring to the mechanism of the CZNPs as seen under the SEM, FIGS. 12A-12B depicts the mechanistic effect of CZNPs acting on Gram-positive *E. faecium* bacteria. ZnO is shown entering the cell through the cell membrane in the bacterium in FIG. 12A, whereas the bacterium in FIG. 12B is completely filled with ZnO. The ZnO will then generate reactive oxygen species, which can then impact the bacterial cell wall, in turn causing loss of the proton motive force and causing the uptake of toxic dissolved ions.

Figure 13:
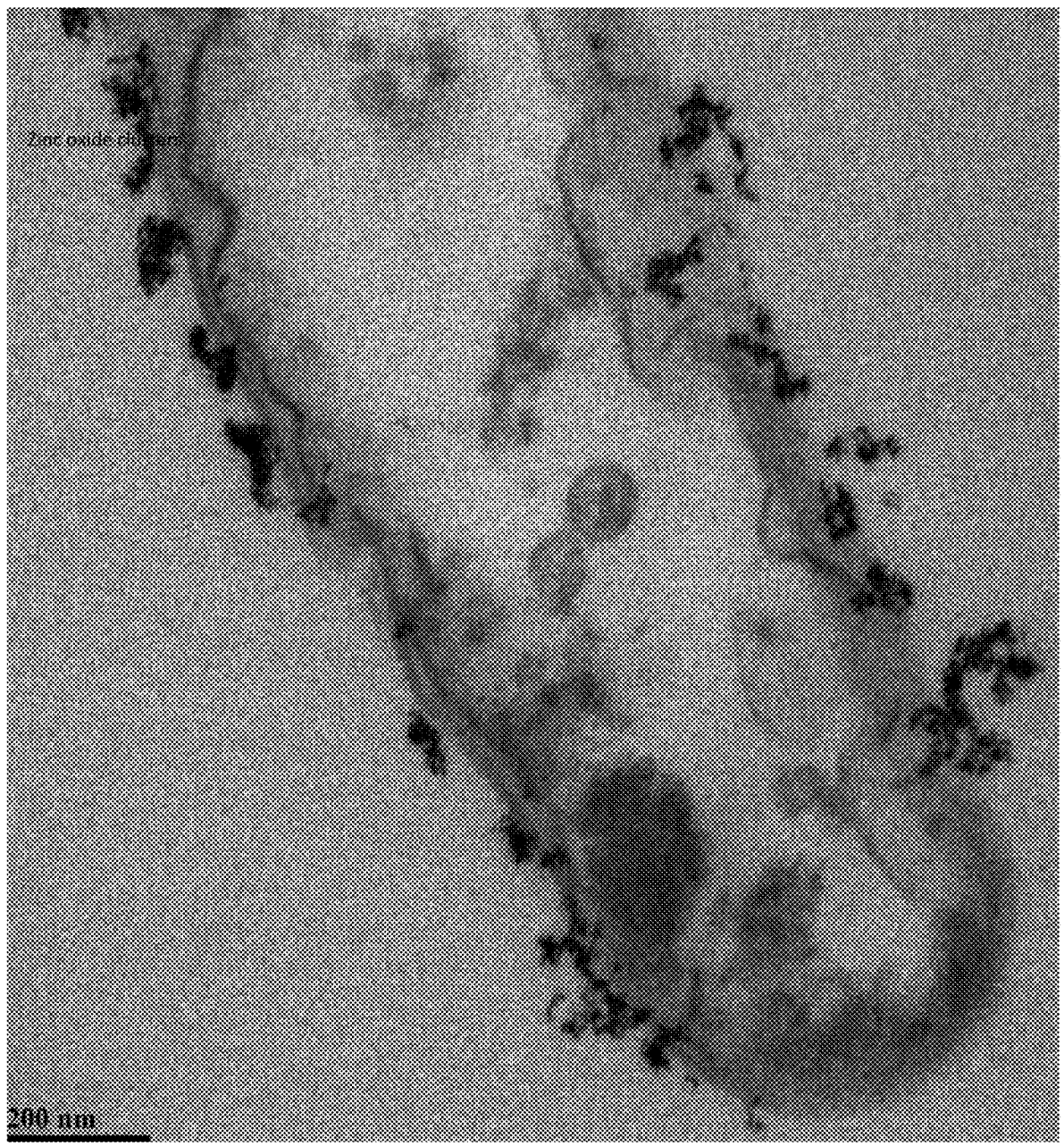
FIG. 13 an SEM image of CZNPs surrounding Gram-negative *E. coli* BAA-2471 bacterial membrane.

Further, FIG. 13 depicts the mechanistic effect of CZNPs acting on Gram-negative bacteria. The CZNPs are clustering on the outside of the bacterial membrane. Cationic chitosan interacts with the negatively charged microbial cell wall, inhibiting microbial activity in a two-fold manner: (1) by promoting changes in cell membrane permeability, leading to internal osmotic imbalances, and (2) by the hydrolysis of the peptidoglycans in the cell wall, leading to the leakage of low molecular weight intracellular components.

Figures 14A, 14B:
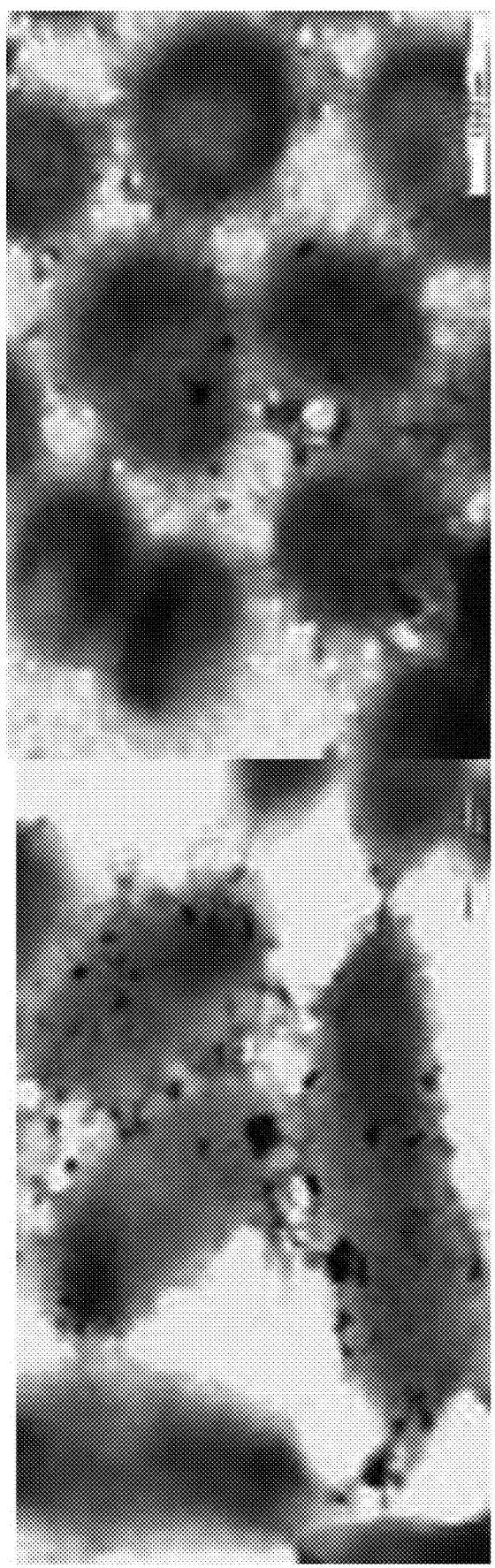
FIG. 14A depicts mechanistic effects of CZNPs on Gram-negative biofilm.
FIG. 14B depicts mechanistic effects of CZNPs on Gram-positive biofilm.

Now adding a time element, FIGS. 14A-14B respectively depict the mechanistic effects of CZNPs after 24 hours on Gram-negative (rod-shaped) *Pseudomonas* and Gram-positive (cocci-shaped) *Micrococcus* bacteria, respectively. The collapsing microbial biofilm is shown as the CZNPs lyse the bacteria and the bacteria lose their electron density.

Illustrative Non-limiting Glossary of Terms

About: This term is used herein to refer to approximately or nearly and in the context of a numerical value or range set forth means±15% of the numerical. In an embodiment, the term "about" can include traditional rounding according to significant figures of the numerical value. In addition, the phrase "about 'x' to 'y'" includes "about 'x' to about 'y'".

Administer: This term is used herein to refer to introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

Composition: This term is used herein to refer to a product comprising the specified ingredients, in the specified amounts, as well as any product which results, directly or indirectly, from combination of the specified ingredients in the specified amounts. Generally, the specified ingredients, or pharmaceutically acceptable salts and derivatives thereof, are suitable agents for use in the diagnosis, mitigation, treatment, cure, or prevention of disease in a subject, specifically but not exclusively effective in the treatment of nosocomial infections, when administered in an effective amount to a subject in need thereof.

Therapeutically effective amount: This term is used herein to refer to that amount of active compound or pharmaceutical agent that elicits a response (e.g., inhibition of lytic bacteria) in a system or entity (e.g., wastewater) that is being sought by a researcher or other operator/user. With reference to the treatment of wastewater, a therapeutically effective amount comprises an amount sufficient to cause the inhibition of lytic bacteria and/or to decrease the growth rate of the bacteria.

Pharmaceutically acceptable carrier: This term is used herein to refer to any of the standard pharmaceutically acceptable carriers, such as a solvent, suspending agent or vehicle, for delivering the compound or compounds in question to the mammal. The pharmaceutical compositions of the subject invention can be formulated according to known methods for preparing pharmaceutically useful compositions. The carrier may be liquid or solid and is selected with the planned manner of administration in mind. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, liposomes, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. The carrier can also include any and all other vehicles, coatings, diluents, antibacterial and antifungal agents, isotonic and absorption delaying agents, buffers, carrier solutions, suspensions, colloids, and the like. Formulations are described in a number of sources that are well known and readily available to those skilled in the art. Except insofar as any conventional media or agent is incompatible with the active ingredient, its use in the therapeutic compositions is contemplated. For example, *Remington's Pharmaceutical Sciences* (Martin E W [1995] Easton Pa. Mack Publishing Company, 19$^{th}$ ed.) describes formulations which can be used in connection with the subject invention.

Pharmaceutically acceptable: This term is used herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

Safe and effective amount: This term is used herein to refer to the quantity of a component or composition that is sufficient to yield a desired therapeutic response without undue adverse side effects (such as toxicity, irritation, or allergic response) commensurate with a reasonable benefit/risk ratio when used in the manner of this invention for the treatment of nosocomial infections.

Selectively toxic: This term is used herein to refer to a capability of the combination of the subject compounds to be discriminatory as to which cells to be harmful. For example, a combination of ZnO and chitosan has been shown to be harmful toward multi-drug resistant bacteria, while be non-harmful or minimally harmful to healthy cells.

Therapeutically effective amount: This term is used herein to refer to means that amount of active compound or pharmaceutical agent that elicits the biological or medicinal response in a tissue, system, animal or human that is being sought by a researcher, veterinarian, medical doctor or other clinician. In reference to nosocomial infections or other gastrointestinal infections, a therapeutically effective amount comprises an amount sufficient to cause the infection to subside or heal and/or to decrease the growth rate of the infection, i.e., by treating the underlying multi-drug resistant bacteria. In some embodiments, an effective amount is an amount sufficient to delay development. In some embodiments, an effective amount is an amount sufficient to prevent or delay occurrence and/or recurrence. An effective amount can be administered in one or more doses.

Treat: This term is used herein to refer to obtaining beneficial or desired results (e.g., clinical results if treating an animal), or any measurable mitigation of disease, infection, or toxicity in a subject (e.g., patient) or entity (e.g., wastewater)—including resolution, reduction, halting progression, and/or slowing progression of the disease, infection, or toxicity. Beneficial or desired results include, but are not limited to, any one or more of the following: alleviation of one or more symptoms, diminishment of extent of infection, stabilized (i.e., not worsening) state of infection, preventing or delaying spread (e.g., metastasis) of the infection, preventing or delaying occurrence or recurrence of the infection, delay or slowing of infection progression, amelioration of the infection state. The methods of the invention contemplate any one or more of these aspects of treatment.

Without affecting: This term is used herein to refer to an administered compound not having a measurable effect on non-targeted entities (e.g., algae and its viability) despite being in contact with the administered compound.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A chitosan zinc oxide nanoparticle formulation selectively toxic against multi-drug resistant bacteria, the formulation comprising:
a therapeutically effective amount of chitosan oligomers;
a therapeutically effective amount of zinc oxide nanoparticles; and
a pharmaceutically acceptable carrier;
wherein a synergistic effect of a combination of the chitosan oligomers and the zinc oxide nanoparticles is more selectively toxic against the multi-drug resistant bacteria than the chitosan oligomers alone or the zinc oxide nanoparticles alone.

2. The nanoparticle formulation of claim 1, wherein the pharmaceutically acceptable carrier is a nanomicelle composite.

3. The nanoparticle formulation of claim 2, wherein the nanomicelle composite includes the zinc oxide nanoparticles outlined by a hydrophobic shell formed of anionic lipid micelles with a coating of the chitosan.

4. The nanoparticle formulation of claim 3, wherein the anionic lipid micelles include 1,2-dioleoyl-sn-glycero-3-phosphate.

5. The nanoparticle formulation of claim 1, wherein the zinc oxide nanoparticles are formed of about 80.34% zinc and about 19.6% oxygen.

6. The nanoparticle formulation of claim 1, wherein the zinc oxide nanoparticles have a surface area of about 54 m$^2$/g.

7. The nanoparticle formulation of claim 1, wherein the chitosan oligomers have a molecular weight of between about 3 kDa to about 50 kDa.

8. The nanoparticle formulation of claim 7, wherein the chitosan has a molecular weight of about 10 kDa and a surface area of about 4.56-0.74 m$^2$/gL.

9. The nanoparticle formulation of claim 7, wherein the molecular weight of the chitosan is about 3 kDa.

10. The nanoparticle formulation of claim 1, wherein the nanoparticle formulation has an average minimum inhibitor concentration of about 0.781 mg/mL to about 1.302 mg/mL.

11. The nanoparticle formulation of claim 1, wherein the multi-drug resistant bacteria comprise Gram positive or Gram negative bacteria.

12. The nanoparticle formulation of claim 1, wherein the multi-drug resistant bacteria comprise *Escherichia coli* or *Enterococcus faecium*.

13. The nanoparticle formulation of claim 1, wherein the multi-drug resistant bacteria is selected from the group consisting of: *Pseudomonas aeruginosa, Bacillus pumilus, Bacillus safensis, Cellulosimicrobium cellulans, Micrococcus luteus*, and *Staphylococcus epidermidis*.

* * * * *